United States Patent
Wang et al.

(10) Patent No.: US 12,371,399 B2
(45) Date of Patent: Jul. 29, 2025

(54) N,N-DIHYDROCARBONYL AMINO CARBOXYLIC ACID, PREPARATION METHOD THEREFOR AND USE THEREOF

(71) Applicant: FUJIAN GOLDEN DRAGON RARE EARTH Co., Ltd., Longyan (CN)

(72) Inventors: Yanliang Wang, Fujian (CN); Wentao Xiao, Fujian (CN); Yuyuan Wu, Fujian (CN); Jinchi Lin, Fujian (CN)

(73) Assignee: FUJIAN GOLDEN DRAGON RARE EARTH Co., Ltd., Longyan (CN)

( * ) Notice: Subject to any disclaimer, the term of this patent is extended or adjusted under 35 U.S.C. 154(b) by 602 days.

(21) Appl. No.: 17/639,137

(22) PCT Filed: Jun. 29, 2021

(86) PCT No.: PCT/CN2021/103175
§ 371 (c)(1),
(2) Date: Feb. 28, 2022

(87) PCT Pub. No.: WO2023/272497
PCT Pub. Date: Jan. 5, 2023

(65) Prior Publication Data
US 2023/0331659 A1    Oct. 19, 2023

(51) Int. Cl.
C07C 233/49 (2006.01)
C07C 233/47 (2006.01)
C22B 3/32 (2006.01)
C22B 59/00 (2006.01)

(52) U.S. Cl.
CPC .......... *C07C 233/49* (2013.01); *C07C 233/47* (2013.01); *C22B 3/32* (2021.05); *C22B 59/00* (2013.01)

(58) Field of Classification Search
CPC ....... C07C 233/49; C07C 233/47; C22B 3/32; C22B 59/00
See application file for complete search history.

(56) References Cited

U.S. PATENT DOCUMENTS

| 10,189,803 B2 | 1/2019 | Chong |
| 2017/0008863 A1 | 1/2017 | Chong |

FOREIGN PATENT DOCUMENTS

| CN | 102337404 A | 2/2012 |
| CN | 103068793 A | 4/2013 |
| CN | 109942446 A | 6/2019 |
| CN | 111302963 A | 6/2020 |
| CN | 112574028 A | 3/2021 |
| CN | 112575188 A | 3/2021 |
| EP | 2404892 A | 1/2012 |
| JP | H09118662 A | 5/1997 |

OTHER PUBLICATIONS

Assad et al., Tetrahedron Letters, (2019), v.60, p. 1646-1648.*
International Search Report cited in PCT/CN2021/103175 mailed on Dec. 22, 2021, 12 pages.
European Search Report cited in EP21863068.9, mailed Jul. 13, 2023, 6 pages.
Liu S., "Preparation of β2-Homologous Amino Acids Bearing Polar Side Chains via a Collective Synthesis Strategy", The Journal of Organic Chemistry, (Jan. 10, 2020), 7 pages.
Assad S., "Diastereoselective Conjugate Addition of Organocuprates to N-[4-(Dibenzylaminobutenoyl)]oxazolidinone. Synthesis of Chiral β-Substituted γ-Aminoacids", Tetrahedron Letters, (May 20, 2019), 3 pages.
Zikha A., "Syntheses of Amide Derivatives of DL-β-Carboxy-γ-Aminobutyric Acid", The Journal of Organic Chemistry, (Aug. 1, 1963), 3 pages.
Bell K.H., "A One-Pot Conversion of Cyclic Anhydrides to Ethyl ω-Dialkylaminoalkanoates", Synthetic Communications, (Dec. 31, 1987), 7 pages.
Chen, et al., "Synthesis of Pregabalin", Chinese journal of Pharmaceuticals, 2004, 2 pages.

* cited by examiner

*Primary Examiner* — Yong L Chu
(74) *Attorney, Agent, or Firm* — PABST PATENT GROUP LLP

(57) ABSTRACT

The present application provides an N,N-dihydrocarbonyl amino carboxylic acid, preparation method therefor and use thereof. The N,N-dihydrocarbonyl amino carboxylic acid can be used as an extractant for enriching rare earth elements from raw materials containing low-concentration rare earth elements, separating and purifying yttrium element from a mixed rare earth raw material, and separating elements such as aluminum, iron, radioactive thorium, radioactive uranium and actinide from a mixed rare earth raw material, etc. The compound can be synthesized in a simple and cost-efficient way. As an extractant, it has good chemical stability and has good resistance against strong acid and strong alkali without decomposition.

23 Claims, No Drawings

N,N-DIHYDROCARBONYL AMINO CARBOXYLIC ACID, PREPARATION METHOD THEREFOR AND USE THEREOF

TECHNICAL FIELD

The present invention belongs to the technical field of synthesis of organic compounds, and relates to an N,N-dihydrocarbonyl amino carboxylic acid, preparation method therefor and use thereof.

BACKGROUND

Rare earth elements refer to 17 metal elements including 15 lanthanides having atomic numbers from 57 to 71 in the periodic table of elements, and scandium with atomic number of 21 and yttrium with atomic number of 39, which have similar chemical properties with lanthanides. Rare earth elements have unique magnetic, optical and electrical properties, and are known as "industrial vitamins". They are widely used in metallurgy, petrochemical industry, glass ceramics, energy materials, military industry and other fields, and are important fundamental raw materials for the development of human society.

At present, the mining of rare earth minerals in nature comprises steps of: leaching rare earth ions with leaching agent to obtain rare earth leachate, and then extracting and separating rare earth ions one by one through solvent extraction. The development of extractant is the core technology of solvent extraction process, and the extractant for rare earth metal used in industry needs to be considered in terms of many factors, such as extraction selectivity, extraction rate, extraction capacity, stability of the compound, solubility, back extraction performance, safety, synthesis method and source, etc. An excellent extractant is one in a million, and a good extractant can simplify production process, improve separation efficiency, reduce production cost and reduce pollution discharge.

Commercially available extractant products known in the field mainly include organic phosphine extractants, carboxylic acid extractants and amine extractants. Typical organic phosphine extractants include 2-ethylhexylphosphonic acid mono(2-ethyl hexyl)ester (P507), di(2-ethylhexyl) phosphonic acid (P204), di(2,4,4-trimethylpentyl) phosphinic acid (C272) and tributyl phosphonate (TBP), and the like, the amine extractants include tri-n-octylamine (N235), secondary carbon primary amine (N1923), methyl trioctyl ammonium chloride (N263) and the like, and the carboxylic acid extractants include naphthenic acid, neodecanoic acid, secondary octyl phenoxyacetic acid (CA-12) and the like.

Commercially available extractants still have some shortcomings. For example, P507 is the most widely used extractant in rare earth separation industry, but its separation coefficient for adjacent rare earth elements is low. For example, the separation coefficient for praseodymium and neodymium is only 1.4, which makes it difficult to separate praseodymium and neodymium elements. Naphthenic acid is mainly used to separate and purify yttrium oxide. However, naphthenic acid is a by-product of petrochemical industry, and its composition is complex, so rare earth elements can be extracted under higher pH conditions. After long-term use, its composition is easy to change, which leads to the decrease of organic phase concentration and affects the stability of separation process. CA-12 extractant has been tried to replace naphthenic acid, which can effectively separate yttrium from all lanthanides in the extraction and separation process of rare earth elements and can overcome the problem that the concentration of organic phase decreases when yttrium is extracted and separated by naphthenic acid. However, the separation coefficient for heavy rare earth elements and yttrium in the extraction system is low, which makes it difficult to separate heavy rare earth elements from yttrium, so it is necessary to design more stages of extraction tanks to achieve the separation effect.

In order to separate rare earth elements more effectively, it is necessary to develop a new extractant having higher separation coefficient compared with the prior art and can overcome the shortcomings in the prior art, and an extraction separation method using thereof.

SUMMARY OF THE INVENTION

An object of the present invention is to provide an N,N-dihydrocarbonyl amino carboxylic acid, preparation method therefor and use thereof. N,N-dihydrocarbonyl amino carboxylic acid can be used as an extractant for separating and purifying selected rare earth elements from a mixed rare earth feed liquid, especially for extracting and separating yttrium element from a mixture containing rare earth elements.

In order to achieve the above object, the present application adopts the following technical solution:

In a first aspect, the present application provides an N,N-dihydrocarbonyl amino carboxylic acid with a structure represented by the following Formula I:

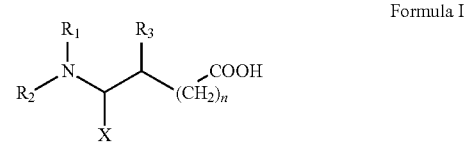

Formula I wherein, $R_1$ and $R_2$ are each independently a linear or branched, saturated or unsaturated, and substituted or unsubstituted C7 or more (for example, C7, C8, C9, C10, C11, C12, C13, C14, C15, C16, C17, C18, C19, C20, C22, C24, C26, C28, C30, C35, C40, etc.) hydrocarbonyl;

$R_3$ is a linear or branched, saturated or unsaturated, and substituted or unsubstituted hydrocarbonyl;

X is H or OH;

n is a natural number from 1 to 10 (for example, 1, 2, 3, 4, 5, 6, 7, 8, 9, 10, etc.).

The present application provides an amino carboxylic acid compound with a structure represented by Formula I as a carboxylic acid extractant for separating rare earth elements and an extraction separation method using the same. This kind of compound has not been reported as extractant for rare earth elements. As an extractant, this kind of compound has high separation coefficient for rare earth elements, especially for separating heavy rare earth elements and yttrium element, and can overcome the shortcomings of naphthenic acid in separating yttrium.

Optionally, the hydrocarbonyl in the present application is any one selected from the group consisting of substituted alkyl, substituted alkenyl and substituted alkynyl, wherein the substituents of the substituted alkyl, the substituted alkenyl and the substituted alkynyl are each independently any one or a combination of at least two selected from the group consisting of halogen, hydroxyl, carboxyl, acyl, ester group, ether group, alkoxy, phenyl, phenoxy, amino, amide, nitro, cyano, thiol, sulfonyl, thioalkyl group, imino, sulfonyl and sulfanyl. Optionally, the substituents are each independently halogen.

Optionally, $R_1$ and $R_2$ are each independently a linear or branched, saturated or unsaturated, and substituted or unsubstituted C7-C30 hydrocarbonyl; optionally a linear or branched, saturated or unsaturated, and substituted or unsubstituted C7-C18 hydrocarbonyl.

Optionally, $R_1$ and $R_2$ are each independently a linear or branched, saturated or unsaturated, and substituted or unsubstituted C7 or more hydrocarbonyl, such as linear or branched, and unsubstituted (C7, C8, C9, C10, C11, C12, C13, C14, C15, C16, C17, C18, C19, C20, C22, C24, C26, C28, C30, C35, C40, etc.) alkyl, alkenyl, alkynyl; optionally a branched, saturated or unsaturated, and unsubstituted C7-C30 hydrocarbonyl; more preferably a branched, saturated or unsaturated, and unsubstituted C7-C12 hydrocarbonyl.

Optionally, $R_1$ and $R_2$ are each independently a linear or branched, and unsubstituted C7-C30 alkyl; optionally a linear or branched, and unsubstituted C7-C18 alkyl; and optionally a linear or branched, and unsubstituted C7-C10 alkyl.

Optionally, X is H; more optionally, n is a natural number from 1 to 6.

Optionally, $R_1$ and $R_2$ are each independently

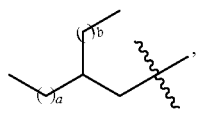

wherein, $3 \leq a+b \leq 10$, 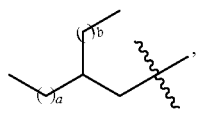 represents a connecting site.

Optionally, $R_1$ and $R_2$ are independently any one selected from the group consisting of the following groups, wherein, represent a connecting site,

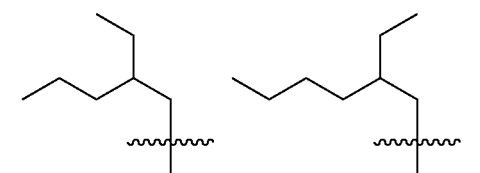

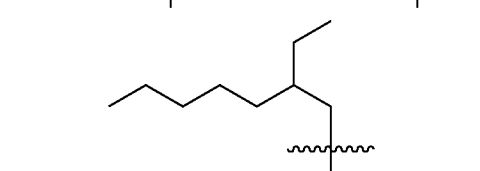

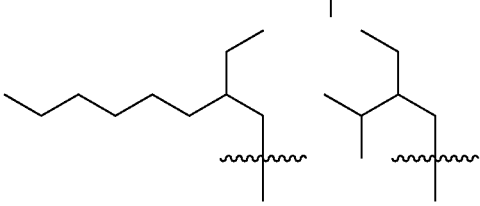

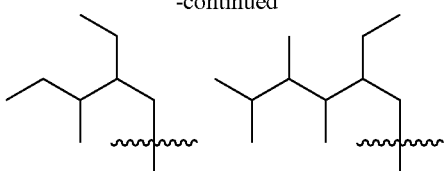

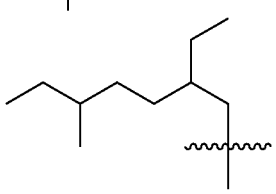

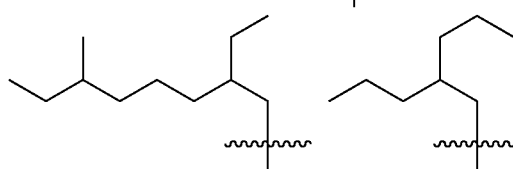

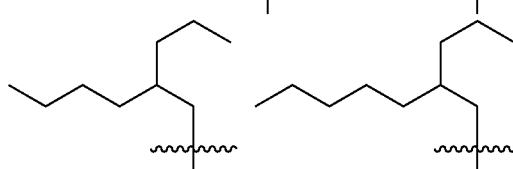

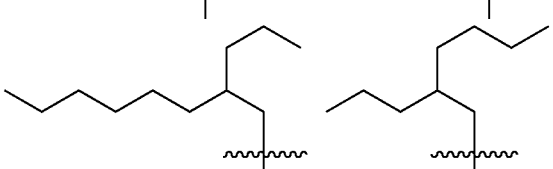

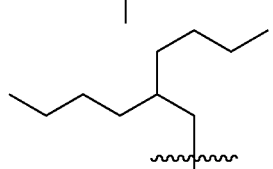

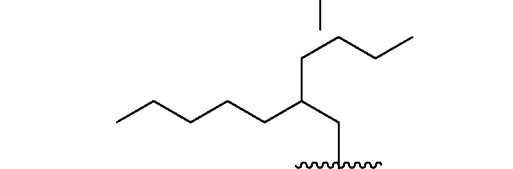

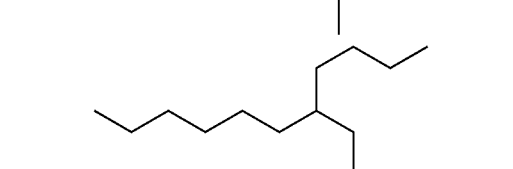

Optionally, $R_3$ is selected from a linear or branched, saturated or unsaturated, and substituted or unsubstituted C6 or more (such as, C6, C7, C8, C9, C10, C11, C12, C13, C14, C15, C16, C17, C18, C19, C20, C30, C40, etc.) hydrocarbonyl; optionally linear or branched, saturated or unsaturated, and substituted or unsubstituted C6-C30 hydrocarbonyl.

Optionally, $R_3$ is selected from a linear or branched, unsaturated and unsubstituted C6 or more (such as, C6, C7, C8, C9, C10, C11, C12, C13, C14, C15, C16, C17, C18, C19, C20, etc.) hydrocarbonyl; optionally a linear C10 or more alkenyl; and more optionally linear C10-C18 alkenyl.

Optionally, $R_3$ is any one selected from the group consisting of the following groups, wherein, ⌇ represent a connecting site,

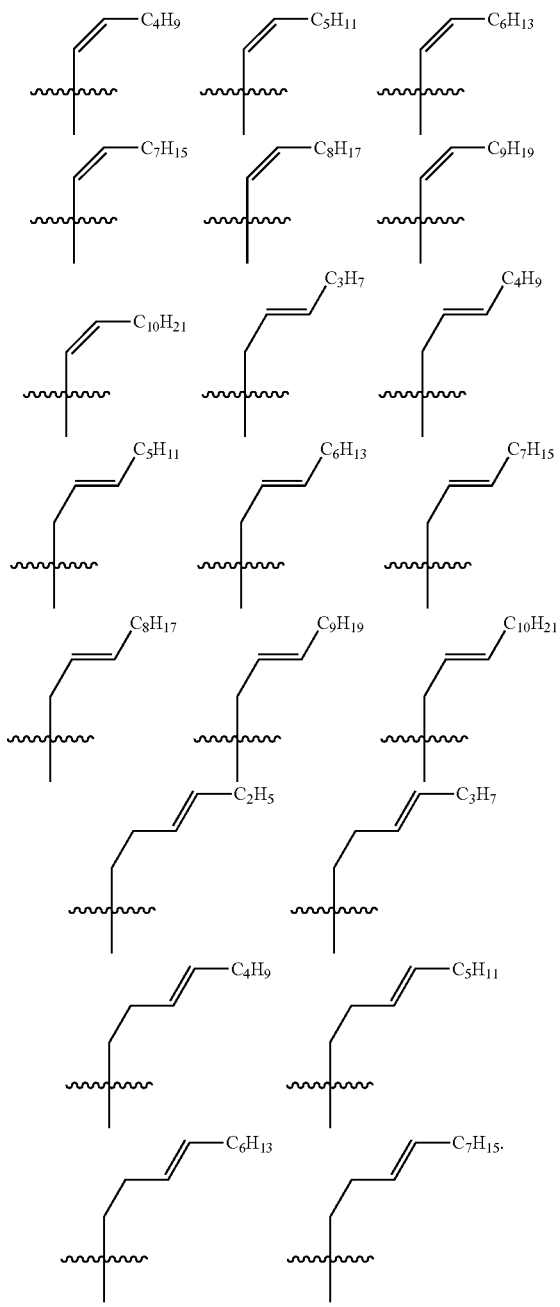

In a second aspect, the present application provides a method for preparing N,N-dihydrocarbonyl amino carboxylic acid according to the first aspect, comprising steps of:
mixing and reacting N,N-dihydrocarbonyl secondary amine represented by Formula II and anhydride compound represented by Formula III to obtain N,N-dihydrocarbonyl amide carboxylic acid represented by Formula IV, and then reducing thus obtained product with reducing agent to obtain N,N-dihydrocarbonyl amino carboxylic acid represented by Formula I, as shown in the following Reaction Scheme:

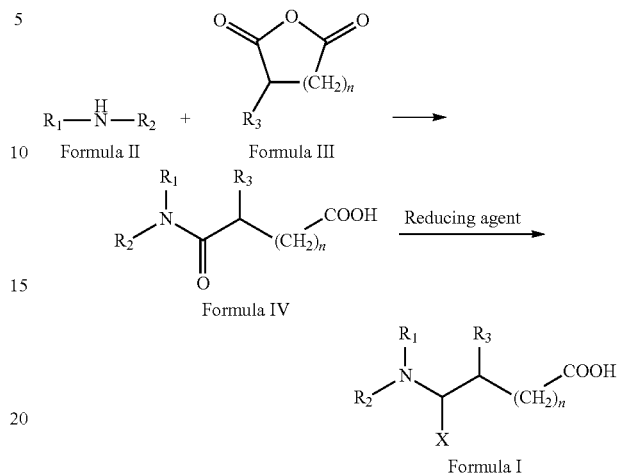

wherein, $R_1$, $R_2$ and $R_3$ are as defined in the first aspect, and n is a natural number from 1 to 10; X is H or OH.

Optionally, the molar ratio of N,N-dihydrocarbonyl secondary amine represented by Formula II to anhydride compound represented by Formula III is 1:(0.8-1.2). For example, it may be 1:0.8, 1:0.9, 1:1, 1:1.1, 1:1.2, etc.

Optionally, the N,N-dihydrocarbonyl secondary amine represented by Formula II and the anhydride compound represented by Formula III are mixed and reacted at temperature of the 0 to 125° C., such as 0° C., 5° C., 10° C., 15° C., 20° C., 25° C., 30° C., 35° C., 40° C., 50° C., 60° C., 70° C., 80° C., 90° C., 95° C., 100° C., 105° C., 110° C., 115° C., 120° C., 125° C., etc. The reaction time is 0.5 to 4 h, such as 0.5 h, 0.6 h, 0.8 h, 1 h, 1.2 h, 1.4 h, 1.6 h, 1.8 h, 2 h, 2.2 h, 2.4 h, 2.6 h, 2.8 h, 3 h, 3.2 h, 3.4 h, 3.6 h, 3.8 h, 4 h, etc.

Optionally, N,N-dihydrocarbonyl secondary amine represented by Formula II and anhydride compound represented by Formula III are mixed and reacted in the absence of a solvent; or in an inert solvent.

In the present application, it is worth mentioning that the reaction can also be carried out in the absence of a solvent, and the compound with the structure represented by Formula II and the compound with the structure represented by Formula III are directly mixed and reacted.

Optionally, the inert solvent is selected from any one or a combination of at least two selected from the group consisting of hexane, dichloromethane, petroleum ether, toluene, xylene or kerosene.

In a third aspect, the present application provides use of the N,N-dihydrocarbonyl amino carboxylic acid according to the first aspect in preparing an extractant for separating rare earth elements.

Optionally, the separating rare earth elements specifically refers to extracting and separating yttrium element from a mixture of rare earth elements.

Compared with the related art, the present application at least has the following advantageous effects.

(1) The amino carboxylic acid provided by the present application can be used for enriching rare earth elements from raw materials containing low-concentration rare earth elements, separating and purifying yttrium element from mixed rare earth raw material, removing elements such as aluminum, iron, radioactive thorium, radioactive uranium and actinide from mixed rare earth raw material, etc., and other fields.

(2) The amino carboxylic acid provided by the present application has good chemical stability and has good resistance to strong acid and strong alkali without decomposition.

MODE OF CARRYING OUT THE INVENTION

In the following, the technical solution of the present application will be further explained with reference to specific embodiments. It should be understood to those skilled in the art that the detailed description is intended to aid in the understanding of the present application, and should not be regarded as a specific limitation of the present application.

Example 1

The present Example provides a compound I-1 represented by Formula I, which has a structural Formula as follows:

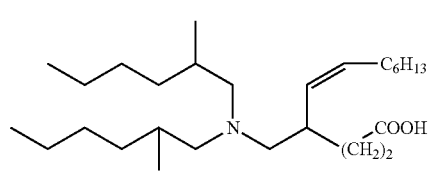

Compound I-1 was prepared by the synthesis route as follows:

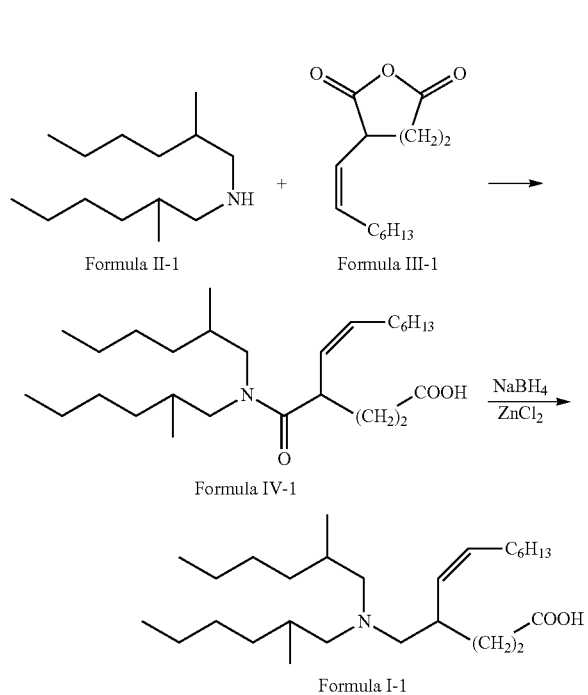

The synthesis method was as follows:

(1) N,N-diheptyl secondary amine represented by Formula II-1 (21.4 g, 0.10 mol) was dissolved in toluene (20 mL) to obtain solution 1; octenyl glutaric anhydride compound represented by Formula III-1 (22.5 g, 0.10 mol) was dissolved in toluene (30 mL) to obtain solution 2;

(2) the solution 1 was added into the solution 2, the thus obtained mixture was stirred while heating to 80° C. and then kept at 80° C. for two hours; after the reaction was finished, toluene was removed by concentrating in vacuum to obtain compound IV-1;

(3) compound IV-1 was reduced in tetrahydrofuran solution dissolved with sodium borohydride ($NaBH_4$) and $ZnCl_2$ to obtain compound I-1.

In the present application, compound I-1 was analyzed by NMR:

$^1$H NMR (500 MHz, $CDCl_3$), δ 12.01 (1H), 5.42 (1H), 5.34 (1H), 2.46 (2H), 2.40 (4H), 2.33 (2H), 2.03 (1H), 1.94 (2H), 1.54 (2H), 1.45 (4H), 1.33 (2H), 1.31 (4H), 1.31 (2H), 1.31 (2H), 1.29 (2H), 1.25 (4H), 1.19 (4H), 0.93 (6H), 0.88 (3H), 0.88 (6H).

$^{13}$C NMR (500 MHz, $CDCl_3$), δ 178.4, 134.9, 129.3, 64.6, 64.4 (2C), 34.8 (2C), 31.9, 31.6, 31.3 (2C), 31.2, 29.9, 29.4, 29.0 (2C), 28.0, 27.5, 23.0 (2C), 22.7, 18.7 (2C), 14.1, 14.1 (2C).

Example 2

The present Example provides a compound I-2 represented by Formula I, which has a structural Formula as follows:

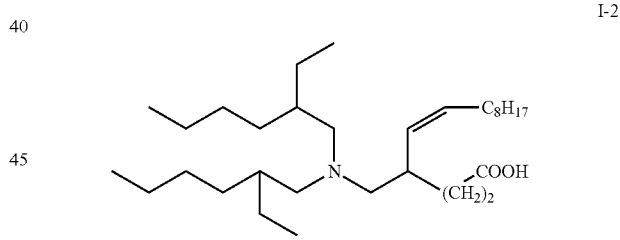

Compound I-2 was prepared by the synthesis route as follows:

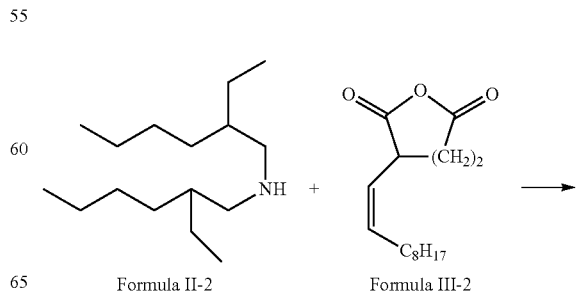

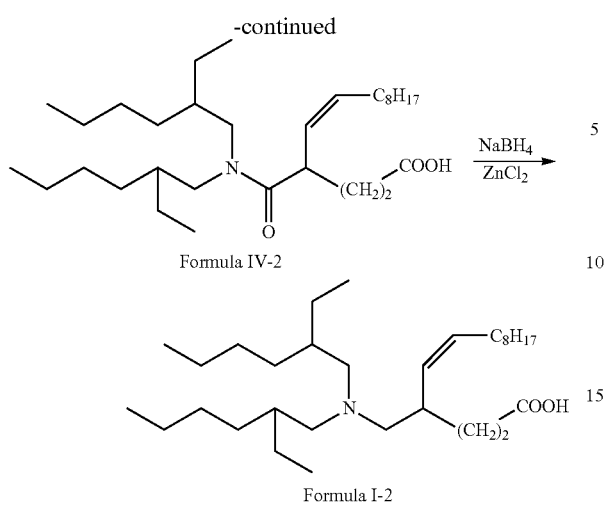

Formula IV-2

Formula I-2

The synthesis method was as follows:

(1) N,N-diisooctyl secondary amine represented by Formula II-2 (24.1 g, 0.10 mol) was dissolved in toluene (20 mL) to obtain solution 1; decenyl glutaric anhydride compound represented by Formula III-2 (25.2 g, 0.10 mol) was dissolved in toluene (30 mL) to obtain solution 2;

(2) the solution 1 was added into the solution 2, and the thus obtained mixture was stirred while heating to 80° C. and then kept at 80° C. for 1 hour; after the reaction was finished, toluene was removed by concentrating in vacuum to obtain compound IV-2;

(3) Compound IV-2 was reduced in tetrahydrofuran solution dissolved with sodium borohydride (NaBH$_4$) and ZnCl$_2$ to obtain compound I-2.

In the present application, compound I-2 was analyzed by NMR:

$^1$H NMR (500 MHz, CDCl$_3$), δ 12.01 (1H), 5.42 (1H), 5.34 (1H), 2.46 (2H), 2.40 (4H), 2.33 (2H), 2.03 (1H), 1.94 (2H), 1.55 (2H), 1.54 (2H), 1.33 (2H), 1.31 (4H), 1.30 (2H), 1.29 (2H), 1.26 (2H), 1.26 (2H), 1.26 (2H), 1.25 (2H), 1.25 (4H), 1.19 (4H), 0.99 (6H), 0.88 (3H), 0.88 (6H).

$^{13}$C NMR (500 MHz, CDCl$_3$), δ 178.4, 134.9, 129.3, 64.6, 63.1 (2C), 38.0 (2C), 32.3 (2C), 31.9, 31.6, 31.2, 29.9, 29.7, 29.3, 29.3 (2C), 28.0, 27.5, 26.3 (2C), 22.7, 14.1, 14.1 (2C), 11.6 (2C).

Example 3

The present Example provides a compound I-3 represented by Formula I, which has a structural Formula as follows:

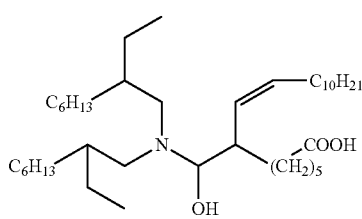

I-3

Compound I-3 was prepared by the synthesis route as follows:

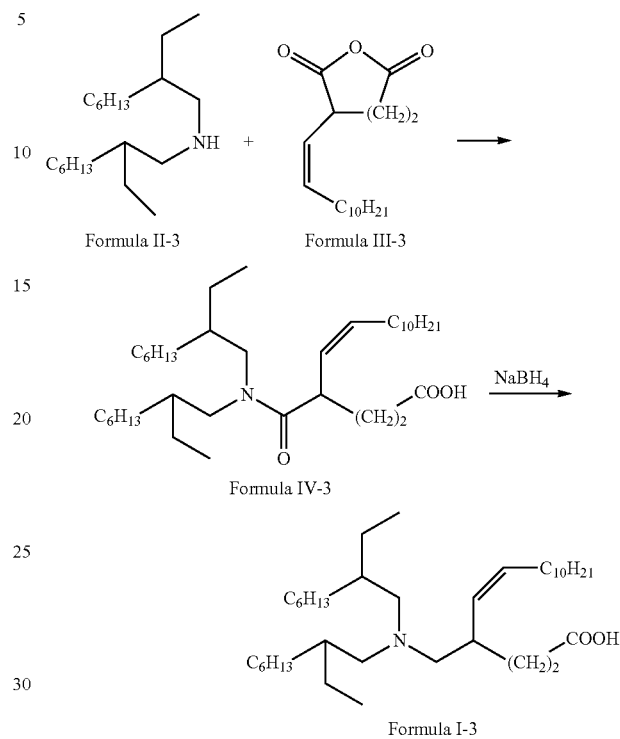

Formula II-3    Formula III-3

Formula IV-3

Formula I-3

The synthesis method was as follows:

(1) N,N-diisodecyl secondary amine represented by Formula II-3 (29.8 g, 0.10 mol) was dissolved in toluene (20 mL) to obtain solution 1; dodecenyl pimelic anhydride compound represented by Formula III-3 (32.2 g, 0.10 mol) was dissolved in toluene (30 mL) to obtain solution 2;

(2) the solution 1 was added into the solution 2, and the thus obtained mixture was stirred while heating to 80° C. and then kept at 80° C. for 1 hour; after the reaction was finished, toluene was removed by concentrating in vacuum to obtain compound IV-3;

(3) compound IV-3 was reduced in tetrahydrofuran solution dissolved with sodium borohydride (NaBH$_4$) to obtain compound I-3.

In the present application, compound I-3 was analyzed by NMR:

$^1$H NMR (500 MHz, CDCl$_3$), δ 11.87 (1H), 5.42 (1H), 5.34 (1H), 5.31 (1H), 4.66 (1H), 2.40 (4H), 2.21 (2H), 2.03 (1H), 1.94 (2H), 1.55 (4H), 1.54 (2H), 1.33 (2H), 1.30 (2H), 1.30 (2H), 1.29 (2H), 1.26 (2H), 1.26 (2H), 1.26 (2H), 1.26 (2H), 1.26 (4H), 1.26 (4H), 1.25 (2H), 1.25 (2H), 1.25 (2H), 1.25 (2H), 1.25 (4H), 1.25 (4H), 1.19 (4H), 0.99 (6H), 0.88 (3H), 0.88 (6H).

$^{13}$C NMR (500 MHz, CDCl$_3$), δ 178.4, 133.5, 132.4, 55.7 (2C), 29.6, 95.0, 38.3 (2C), 37.5, 34.0, 32.6 (2C), 31.8 (2C), 31.9, 29.9, 29.6 (2C), 29.7, 29.7, 29.6, 29.4, 29.3, 28.0, 27.2, 27.1 (2C), 27.0, 26.3 (2C), 24.7, 22.7 (2C), 22.7, 14.1 (2C), 14.1, 11.6 (2C).

Example 4

The present Example provides a compound I-4 represented by Formula I, which has a structural Formula as follows:

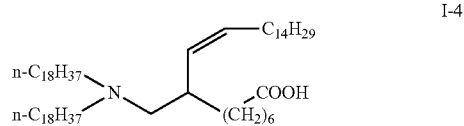

Compound I-4 was prepared by the synthesis route as follows:

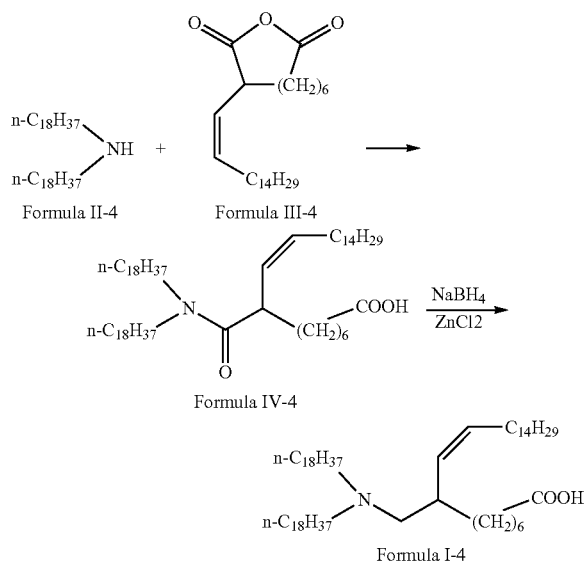

The synthesis method was as follows:
(1) N,N-dioctadecyl secondary amine represented by Formula II-4 (52.1 g, 0.10 mol) was dissolved in toluene (20 mL) to obtain solution 1; hexadecenyl azelaic anhydride compound represented by Formula III-4 (37.8 g, 0.10 mol) was dissolved in toluene (30 mL) to obtain solution 2;
(2) the solution 1 was added into the solution 2, and the thus obtained mixture was stirred while heating to 80° C. and then kept at 80° C. for 1 hour; after the reaction was finished, toluene was removed by concentrating in vacuum to obtain compound IV-4;
(3) compound IV-4 was reduced in tetrahydrofuran solution dissolved with sodium borohydride ($NaBH_4$) and $ZnCl_2$ to obtain compound I-4.

In the present application, compound I-4 was analyzed by NMR:

$^1$H NMR (500 MHz, $CDCl_3$), δ11.87 (1H), 5.42 (1H), 5.34 (1H), 2.46 (2H), 2.43 (4H), 2.21 (2H), 2.03 (1H), 1.94 (2H), 1.54 (2H), 1.36 (4H), 1.33 (2H), 1.33 (2H), 1.30 (2H), 1.30 (2H), 1.29 (2H), 1.29 (4H), 1.27 (4H), 1.26 (48H), 1.26 (4H), 1.26 (16H), 1.25 (2H), 1.25 (2H), 1.25 (2H), 0.88 (3H), 0.88 (6H).

$^{13}$C NMR (500 MHz, $CDCl_3$), δ 178.4, 133.5, 132.4, 64.3, 57.6 (2C), 34.0, 33.2, 32.2, 31.9, 31.9 (2C), 29.9, 29.7, 29.7, 29.7, 29.6 (6C), 29.6 (20C), 29.3, 29.3 (2C), 29.3 (2C), 29.0, 28.3 (2C), 28.0, 27.3 (2C), 27.2, 24.7, 22.7, 22.7 (2C), 14.1, 14.1 (2C).

Example 5

The present Example provides a compound I-5 represented by Formula I, which has a structural Formula as follows:

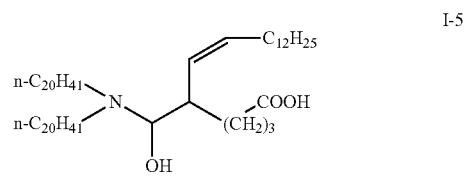

Compound I-5 was prepared by the synthesis route as follows:

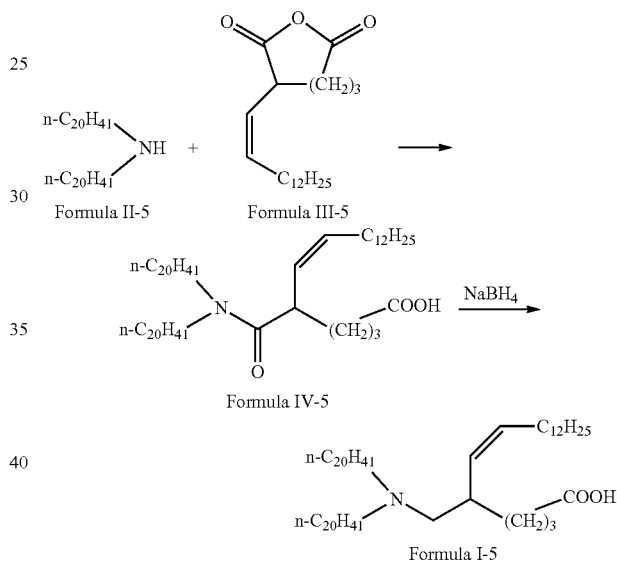

The synthesis method was as follows:
(1) N,N-dieicosyl secondary amine represented by Formula II-5 (57.8 g, 0.10 mol) was dissolved in toluene (20 mL) to obtain solution 1; dodecenyl adipic anhydride compound represented by Formula III-5 (29.4 g, 0.10 mol) was dissolved in toluene (30 mL) to obtain solution 2;
(2) the solution 1 was added into the solution 2, and the thus obtained mixture was stirred while heating to 80° C. and then kept at 80° C. for 1 hour; after the reaction was finished, toluene was removed by concentrating in vacuum to obtain compound IV-5;
(3) compound IV-5 was reduced in tetrahydrofuran solution dissolved with sodium borohydride ($NaBH_4$) to obtain compound I-5.

In the present application, compound I-5 was analyzed by NMR:

$^1$H NMR (500 MHz, $CDCl_3$), δ 11.87 (1H), 5.42 (1H), 5.34 (1H), 5.31 (1H), 4.66 (1H), 2.43 (4H), 2.33 (2H), 2.03 (2H), 1.94 (2H), 1.54 (2H), 1.37 (4H), 1.33 (2H), 1.30 (2H), 1.30 (2H), 1.29 (2H), 1.29 (4H), 1.27 (4H), 1.26 (4H), 1.26 (8H), 1.26 (56H), 1.25 (2H), 0.88 (3H), 0.88 (6H).

$^{13}$C NMR (500 MHz, CDCl$_3$), δ 178.4, 133.5, 132.4, 94.4, 51.4 (2C), 37.2, 34.4, 31.9, 31.9 (2C), 29.9, 29.7, 29.7, 29.6, 29.6, 29.6 (24C), 29.3, 29.3 (2C), 29.3 (2C), 28.6 (2C), 28.0, 27.3 (2C), 26.4, 25.5, 22.7, 22.7 (2C), 14.1 (2C), 14.1.

Example 6

The present Example provides a compound I-6 represented by Formula I, which has a structural Formula as follows:

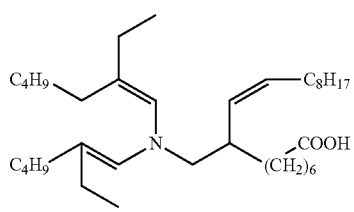

I-6

Compound I-6 was prepared by the synthesis route as follows:

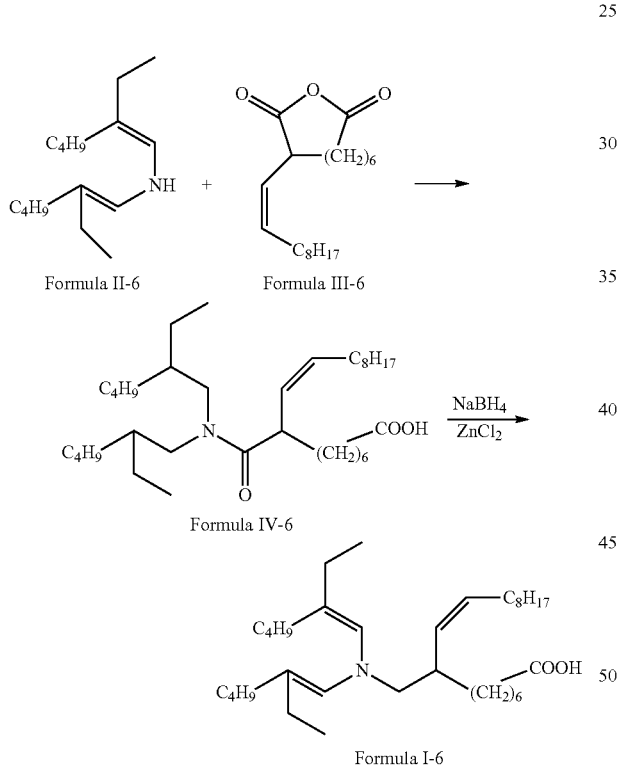

The synthesis method was as follows:
(1) N,N-diisooctenyl secondary amine represented by Formula II-6 (23.8 g, 0.10 mol) was dissolved in toluene (20 mL) to obtain solution 1; decenyl azelaic anhydride compound represented by Formula III-6 (30.8 g, 0.10 mol) was dissolved in toluene (30 mL) to obtain solution 2;
(2) the solution 1 was added into the solution 2, and the thus obtained mixture was stirred while heating to 80° C. and then kept at 80° C. for 1 hour; after the reaction was finished, toluene was removed by concentrating in vacuum to obtain compound IV-6;

(3) compound IV-6 was reduced in tetrahydrofuran solution dissolved with sodium borohydride (NaBH$_4$) and ZnCl$_2$ to obtain compound I-6.

In the present application, compound I-6 was analyzed by NMR:

$^1$H NMR (500 MHz, CDCl$_3$), δ11.87 (1H), 5.92 (1H), 5.42 (1H), 5.34 (1H), 3.23 (2H), 2.21 (2H), 2.18 (4H), 2.03 (1H), 2.00 (4H), 1.94 (2H), 1.54 (2H), 1.38 (4H), 1.33 (2H), 1.33 (2H), 1.30 (2H), 1.29 (2H), 1.29 (4H), 1.26 (2H), 1.26 (2H), 1.26 (2H), 1.25 (2H), 1.25 (2H), 1.25 (2H), 0.93 (6H), 0.88 (3H), 0.85 (6H).

$^{13}$C NMR (500 MHz, CDCl$_3$), δ 178.4, 133.5, 132.4, 124.6 (2C), 116.6 (2C), 62.0, 34.0, 33.4, 32.4, 31.9, 29.9, 29.7, 29.7, 29.7, 29.6 (2C), 29.3, 29.0, 28.3 (2C), 28.0, 28.0 (2C), 27.2, 24.7, 23.1 (2C), 22.7, 11.8 (2C), 14.1, 14.1 (2C).

Example 7

The present Example provides a compound I-7 represented by Formula I, which has a structural Formula as follows:

I-7

Compound I-7 was prepared by the synthesis route as follows:

The synthesis method was as follows:
(1) N,N-diisodecenyl secondary amine represented by Formula II-7 (29.3 g, 0.10 mol) was dissolved in toluene (20 mL) to obtain solution 1; octadecenyl tridecandioic anhydride compound represented by Formula III-7 (47.6 g, 0.10 mol) was dissolved in toluene (30 mL) to obtain solution 2;
(2) the solution 1 was added into the solution 2, and the thus obtained mixture was stirred while heating to 80° C. and then kept at 80° C. for 1 hour; after the reaction was finished, toluene was removed by concentrating in vacuum to obtain compound IV-7;
(3) compound IV-7 was reduced in tetrahydrofuran solution dissolved with sodium borohydride ($NaBH_4$) and $ZnCl_2$ to obtain compound I-7.

In the present application, compound I-7 was analyzed by NMR:

$^1$H NMR (500 MHz, $CDCl_3$), δ 11.87 (1H), 5.92 (2H), 5.42 (1H), 5.34 (1H), 3.23 (2H), 2.21 (2H), 2.18 (4H), 2.03 (1H), 2.00 (4H), 1.94 (2H), 1.54 (2H), 1.33 (2H), 1.33 (2H), 1.33 (4H), 1.31 (4H), 1.31 (4H), 1.30 (2H), 1.30 (2H), 1.30 (2H), 1.29 (2H), 1.29 (4H), 1.26 (2H), 1.26 (2H), 1.26 (2H), 1.26 (20H), 1.25 (2H), 1.25 (2H), 1.25 (2H), 0.88 (3H), 0.88 (6H), 0.85 (6H).

$^{13}$C NMR (500 MHz, $CDCl_3$), δ 178.4, 133.5, 132.4, 124.6 (2C), 116.6 (2C), 62.0, 34.0, 33.4, 32.4, 31.9, 31.9 (2C), 30.0, 29.9, 29.7, 29.7, 29.6 (8C), 29.6, 29.6, 29.6, 29.7 (2C), 29.3, 29.3, 29.0, 28.6 (2C), 28.6 (2C), 28.0, 28.0 (2C), 27.2, 24.7, 22.7, 22.7 (2C), 14.1, 14.1 (2C), 11.8 (2C).

Example 8

The present Example provides a compound I-8 represented by Formula I, which has a structural Formula as follows:

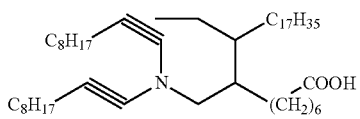

I-8

Compound I-8 was prepared by the synthesis route as follows:

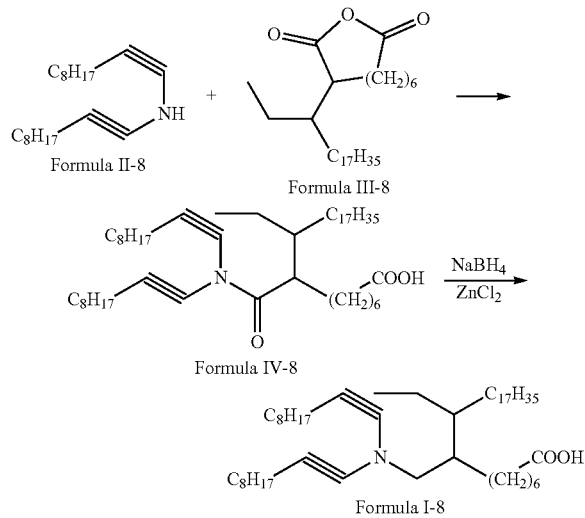

The synthesis method was as follows:
(1) N,N-didecynyl secondary amine represented by Formula II-8 (28.9 g, 0.10 mol) was dissolved in toluene (20 mL) to obtain solution 1; eicosyl azelaic anhydride compound represented by Formula III-8 (45.0 g, 0.10 mol) was dissolved in toluene (30 mL) to obtain solution 2;
(2) the solution 1 was added into the solution 2, and the thus obtained mixture was stirred while heating to 80° C. and then kept at 80° C. for 1 hour; after the reaction was finished, toluene was removed by concentrating in vacuum to obtain compound IV-8;
(3) compound IV-8 was reduced in tetrahydrofuran solution dissolved with sodium borohydride ($NaBH_4$) and $ZnCl_2$ to obtain compound I-8.

In the present application, compound I-8 was analyzed by NMR:

$^1$H NMR (500 MHz, $CDCl_3$), δ 11.87 (1H), 2.69 (2H), 2.46 (4H), 2.21 (2H), 1.55 (2H), 1.54 (2H), 1.44 (4H), 1.33 (2H), 1.29 (4H), 1.26 (4H), 1.26 (4H), 1.26 (4H), 1.26 (4H), 1.26 (26H), 1.25 (2H), 1.25 (2H), 1.25 (2H), 1.25 (2H), 1.19 (2H), 1.19 (2H), 1.15 (1H), 1.10 (1H), 0.99 (3H), 0.88 (3H), 0.88 (6H).

$^{13}$C NMR (500 MHz, $CDCl_3$), δ178.4, 83.3 (2C), 81.9 (2C), 56.6, 34.9, 37.3, 34.0, 31.9, 31.9 (2C), 29.9, 29.6, 29.6 (10C), 29.3, 29.3 (2C), 29.0, 28.9, 28.7 (2C), 28.7 (2C), 28.4 (2C), 28.3, 27.7, 27.4, 24.7, 23.5, 22.7, 22.7 (2C), 15.9 (2C), 12.2, 14.1, 14.1 (2C).

Example 9

The present Example provides a compound I-9 represented by Formula I, which has a structural Formula as follows:

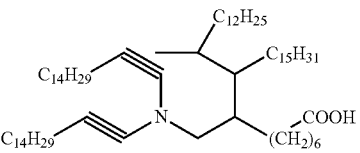

I-9

Compound I-9 was prepared by the synthesis route as follows:

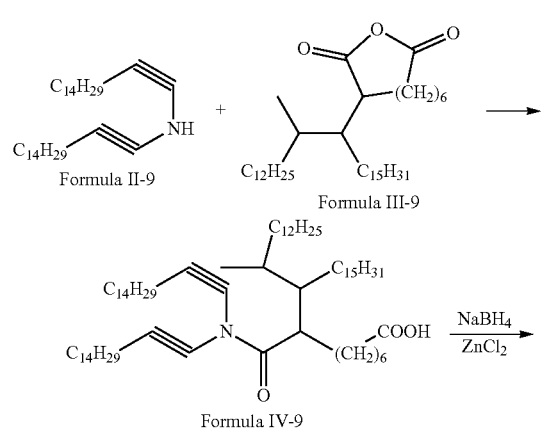

17

-continued

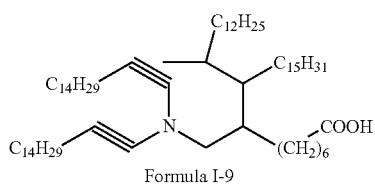

Formula I-9

The synthesis method can be carried out with or without a solvent, and the synthesis method with a solvent was as follows:

(1) N,N-dihexadecynyl secondary amine represented by Formula II-9 (45.8 g, 0.10 mol) was dissolved in toluene (20 mL) to obtain solution 1; myricyl azelaic anhydride compound represented by Formula III-9 (52.0 g, 0.10 mol) was dissolved in toluene (30 mL) to obtain solution 2;

(2) the solution 1 was added into the solution 2, and the thus obtained mixture was stirred while heating to 80° C. and then kept at 80° C. for 1 hour; after the reaction was finished, toluene was removed by concentrating in vacuum to obtain compound IV-9;

(3) compound IV-9 was reduced in tetrahydrofuran solution dissolved with sodium borohydride ($NaBH_4$) and $ZnCl_2$ to obtain compound I-9.

In the present application, compound I-9 was analyzed by NMR:

$^1$H NMR (500 MHz, $CDCl_3$), δ 11.87 (1H), 2.69 (2H), 2.46 (4H), 2.21 (2H), 1.54 (2H), 1.44 (4H), 1.33 (2H), 1.30 (1H), 1.29 (4H), 1.26 (40H), 1.26 (16H), 1.26 (22H), 1.25 (2H), 1.25 (2H), 1.25 (2H), 1.25 (2H), 1.25 (2H), 1.25 (2H), 1.19 (2H), 1.19 (2H), 1.19 (2H), 1.15 (1H), 1.00 (1H), 0.88 (3H), 0.88 (3H), 0.88 (3H), 0.88 (6H).

$^{13}$C NMR (500 MHz, $CDCl_3$), δ 178.4, 83.3 (2C), 81.9 (2C), 56.9, 43.9, 35.5, 35.1, 34.0, 32.7, 31.9, 31.9, 31.9 (2C), 29.9, 29.9, 29.6, 29.6 (5C), 29.6 (8C), 29.6 (12C), 29.3, 29.3, 29.3 (2C), 29.2, 29.0, 28.7 (2C), 28.7 (2C), 28.4 (2C), 28.0, 27.4, 27.4, 26.1, 24.7, 22.7, 22.7, 22.7 (2C), 19.1, 15.9 (2C), 14.1, 14.1, 14.1 (2C).

Example 10

The present Example provides a compound I-10 represented by Formula I, which has a structural Formula as follows:

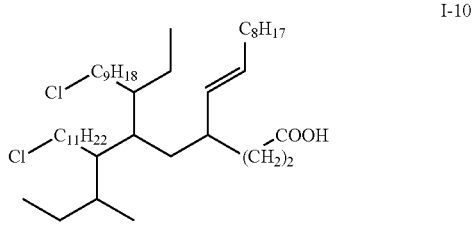

I-10

18

Compound I-10 was prepared by the synthesis route as follows:

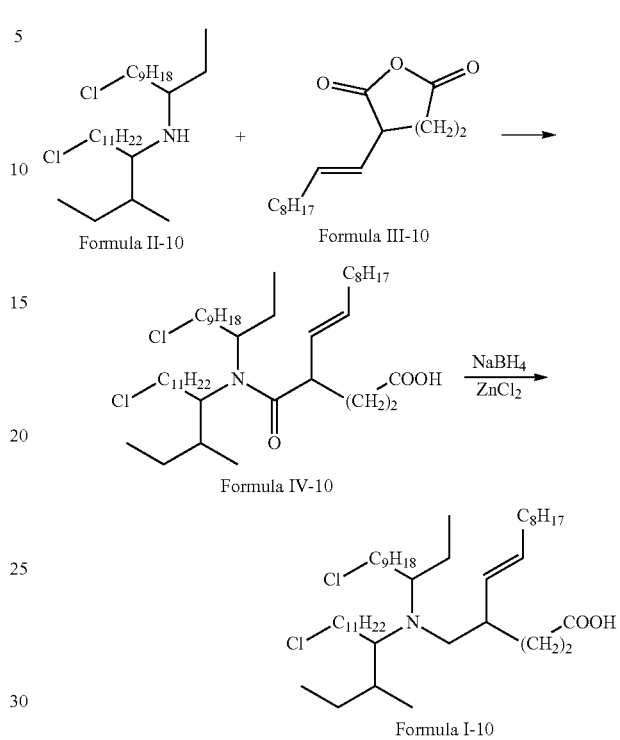

The synthesis method can be carried out with or without a solvent, and the synthesis method with a solvent was as follows:

(1) N,N-dichlorohexadecyl secondary amine represented by Formula II-10 (47.9 g, 0.10 mol) was dissolved in toluene (20 mL) to obtain solution 1; decenyl glutaric anhydride compound represented by Formula III-10 (32.2 g, 0.10 mol) was dissolved in toluene (30 mL) to obtain solution 2;

(2) the solution 1 was added into the solution 2, and the thus obtained mixture was stirred while heating to 80° C. and then kept at 80° C. for 2 hour; after the reaction was finished, toluene was removed by concentrating in vacuum to obtain compound IV-10;

(3) compound IV-10 was reduced in tetrahydrofuran solution dissolved with sodium borohydride ($NaBH_4$) and $ZnCl_2$ to obtain compound I-10.

In the present application, compound I-10 was analyzed by NMR: 1H NMR (500 MHz, $CDCl_3$), δ 12.01 (1H), 5.48 (1H), 5.43 (1H), 3.60 (2H), 3.60 (2H), 2.46 (2H), 2.43 (1H), 2.33 (1H), 2.33 (2H), 2.03 (1H), 1.94 (2H), 1.77 (2H), 1.77 (2H), 1.54 (2H), 1.49 (2H), 1.49 (2H), 1.46 (2H), 1.35 (1H), 1.33 (2H), 1.31 (2H), 1.31 (2H), 1.30 (2H), 1.29 (2H), 1.26 (2H), 1.26 (2H), 1.26 (2H), 1.26 (6H), 1.26 (10H), 1.25 (2H), 1.25 (2H), 1.25 (2H), 1.25 (2H), 0.88 (3H), 0.88 (3H), 0.87 (3H).

$^{13}$C NMR (500 MHz, $CDCl_3$), δ 178.4, 134.9, 129.3, 77.0, 75.5, 59.9, 44.7, 44.7, 40.1, 38.2, 34.0, 32.3, 31.9, 31.3, 31.3, 31.1, 31.2, 29.9, 29.7, 29.7, 29.6, 29.6, 29.6, 29.6, 29.6, 29.6, 29.6, 29.3, 28.8, 28.8, 27.6, 27.5, 27.3, 26.7, 26.3, 26.2, 22.7, 18.5, 16.7, 14.1, 11.6, 11.0.

Example 11

The present Example provides a compound I-11 represented by Formula I, which has a structural Formula as follows:

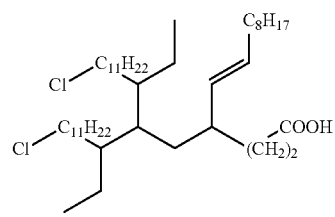

Compound I-11 was prepared by the synthesis route as follows:

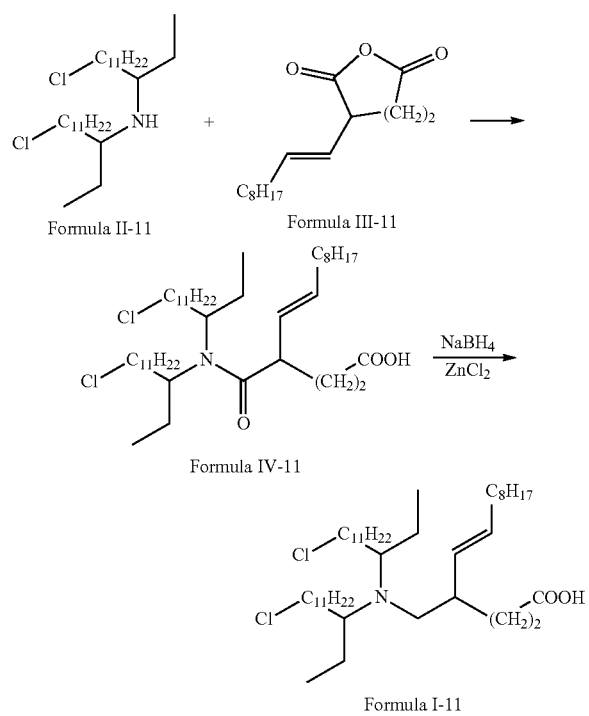

The synthesis method was as follows:
(1) N,N-dichlorotetradecanyl secondary amine represented by Formula II-11 (47.9 g, 0.10 mol) was dissolved in toluene (20 mL) to obtain solution 1; decenyl glutaric anhydride compound represented by Formula III-11 (32.2 g, 0.10 mol) was dissolved in toluene (30 mL) to obtain solution 2;
(2) the solution 1 was added into the solution 2, and the thus obtained mixture was stirred while heating to 80° C. and then kept at 80° C. for 2 hours; after the reaction was finished, toluene was removed by concentrating in vacuum to obtain compound IV-11;
(3) compound IV-11 was reduced in tetrahydrofuran solution dissolved with sodium borohydride ($NaBH_4$) and $ZnCl_2$ to obtain compound I-11.

In the present application, compound I-11 was analyzed by NMR: $^1H$ NMR (500 MHz, $CDCl_3$), δ 12.01 (1H), 5.48 (1H), 5.43 (1H), 3.60 (4H), 2.46 (2H), 2.43 (2H), 2.33 (2H), 2.03 (1H), 1.94 (2H), 1.77 (4H), 1.54 (2H), 1.49 (4H), 1.46 (4H), 1.33 (2H), 1.31 (4H), 1.30 (2H), 1.29 (2H), 1.26 (2H), 1.26 (2H), 1.26 (2H), 1.26 (20H), 1.25 (4H), 1.25 (4H), 0.88 (3H), 0.87 (6H).

$^{13}C$ NMR (500 MHz, $CDCl_3$), δ 178.4, 134.9, 129.3, 75.2 (2C), 59.6, 44.7 (2C), 38.2, 34.0, 32.3 (2C), 31.9, 31.2, 31.1 (2C), 29.9, 29.7, 29.7, 29.6 (10C), 29.3, 28.8 (2C), 27.5, 27.3 (2C), 26.7 (2C), 26.2 (2C), 22.7, 14.1, 11.0 (2C).

Example 12

The present Example provides a compound I-12 represented by Formula I, which has a structural Formula as follows:

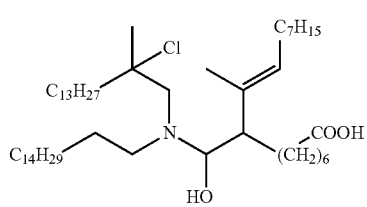

Compound I-12 was prepared by the synthesis route as follows:

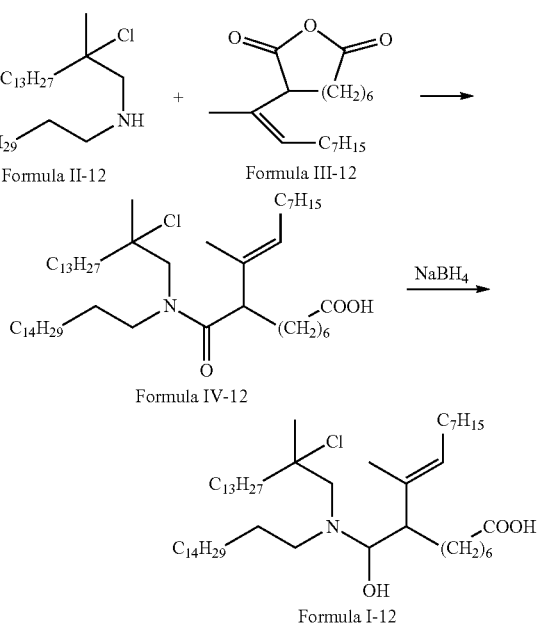

The synthesis method was as follows:
(1) N,N-dialkyl secondary amine represented by Formula II-12 (49.9 g, 0.10 mol) was dissolved in toluene (20 mL) to obtain solution 1; eicosyl azelaic anhydride compound represented by Formula III-12 (30.8 g, 0.10 mol) was dissolved in toluene (30 mL) to obtain solution 2;
(2) the solution 1 was added into the solution 2, and the thus obtained mixture was stirred while heating to 80° C. and then kept at 80° C. for 1 hour; after the reaction was finished, toluene was removed by concentrating in vacuum to obtain compound IV-12;

(3) compound IV-12 was reduced in tetrahydrofuran solution dissolved with sodium borohydride (NaBH₄) to obtain compound I-12.

In the present application, compound I-12 was analyzed by NMR:

$^1$H NMR (500 MHz, CDCl$_3$), δ11.87 (1H), 5.31 (1H), 5.20 (1H), 4.66 (1H), 2.65 (2H), 2.43 (2H), 2.21 (2H), 2.03 (1H), 1.94 (2H), 1.79 (3H), 1.64 (3H), 1.43 (2H), 1.37 (2H), 1.33 (4H), 1.30 (2H), 1.29 (4H), 1.27 (2H), 1.26 (46H), 1.25 (10H), 0.88 (9H).

$^{13}$C NMR (500 MHz, CDCl$_3$), δ178.4, 138.0, 128.9, 91.7, 64.3, 52.9, 51.2, 48.1, 41.5, 34.0, 31.9, 31.9, 31.8, 30.2, 29.7, 29.7, 29.6 (6C), 29.6 (8C), 29.4, 29.4, 29.3, 29.3, 29.3, 29.3, 29.0, 28.6, 27.8, 27.5, 27.3, 24.7, 24.5, 22.7, 22.7, 22.7, 21.7, 15.2, 14.1, 14.1, 14.1.

Example 13

The present Example provides a compound I-13 represented by Formula I, which has a structural Formula as follows:

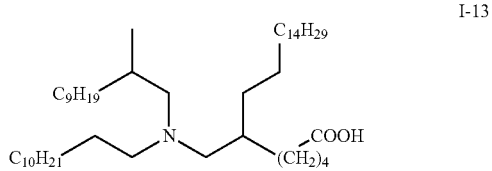

I-13

Compound I-13 was prepared by the synthesis route as follows:

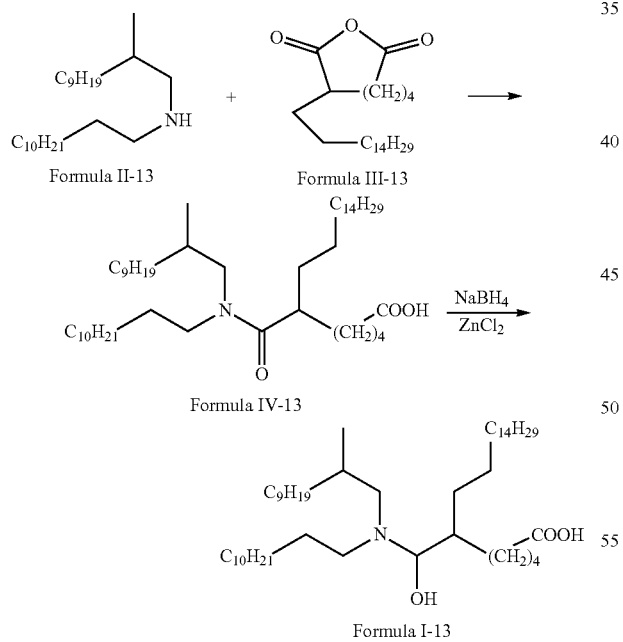

The synthesis method was as follows:
(1) N,N-dialkyl secondary amine represented by Formula II-13 (35.4 g, 0.10 mol) was dissolved in toluene (20 mL) to obtain solution 1; hexadecanyl pimelic anhydride compound represented by Formula III-13 (36.7 g, 0.10 mol) was dissolved in toluene (30 mL) to obtain solution 2;

(2) the solution 1 was added into the solution 2, and the thus obtained mixture was stirred while heating to 80° C. and then kept at 80° C. for 1 hour; after the reaction was finished, toluene was removed by concentrating in vacuum to obtain compound IV-13;

(3) compound IV-13 was reduced in tetrahydrofuran solution dissolved with sodium borohydride-zinc chloride (NaBH₄—ZnCl₂) to obtain compound I-13.

In the present application, compound I-13 was analyzed by NMR:

$^1$H NMR (500 MHz, CDCl$_3$), δ11.87 (1H), 2.43 (2H), 2.40 (2H), 2.40 (2H), 2.21 (2H), 1.54 (2H), 1.45 (1H), 1.36 (2H), 1.29 (2H), 1.27 (2H), 1.26 (24H), 1.26 (24H), 1.25 (4H), 1.25 (2H), 1.25 (1H), 1.25 (4H), 1.19 (2H), 1.19 (2H), 1.19 (2H), 0.93 (3H), 0.88 (9H).

$^{13}$C NMR (500 MHz, CDCl$_3$), δ178.4, 64.0, 63.0, 57.8, 35.8, 35.1, 34.0, 32.9, 32.6, 31.9, 31.9, 31.9, 31.3, 29.9, 29.9, 29.6 (2C), 29.6 (4C), 29.6 (9C), 29.3, 29.3, 29.3, 29.3, 28.3, 27.3, 27.1, 26.8, 26.5, 25.0, 22.7, 22.7, 22.7, 18.7, 14.1, 14.1, 14.1.

Example 14

The present Example provides a compound I-14 represented by Formula I, which has a structural Formula as follows:

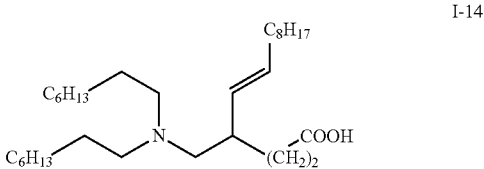

I-14

Compound I-14 was prepared by the synthesis route as follows:

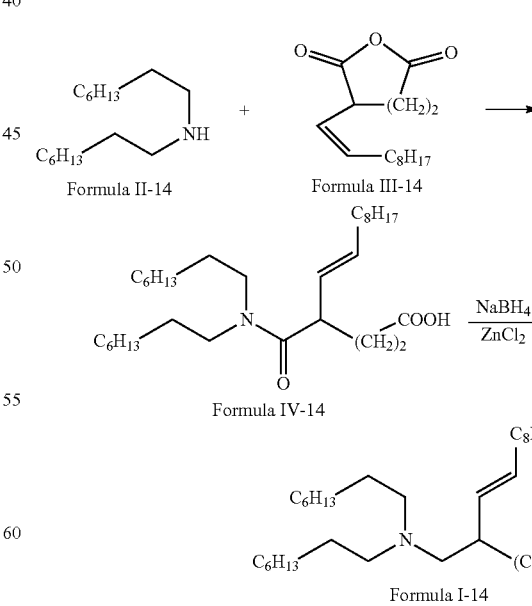

The synthesis method was as follows:
(1) N,N-dialkyl secondary amine represented by Formula II-14 (24.1 g, 0.10 mol) was dissolved in toluene (20 mL) to obtain solution 1; decenyl glutaric anhydride compound represented by Formula III-14 (25.2 g, 0.10 mol) was dissolved in toluene (30 mL) to obtain solution 2;

(2) the solution 1 was added into the solution 2, and the thus obtained mixture was stirred while heating to 80° C. and then kept at 80° C. for 1 hour; after the reaction was finished, toluene was removed by concentrating in vacuum to obtain compound IV-14;

(3) compound IV-14 was reduced in tetrahydrofuran solution dissolved with sodium borohydride-zinc chloride (NaBH$_4$—ZnCl$_2$) to obtain compound I-14.

In the present application, compound I-14 was analyzed by NMR:

$^1$H NMR (500 MHz, CDCl$_3$), δ12.01 (1H), 5.48 (1H), 5.43 (1H), 2.46 (2H), 2.43 (4H), 2.33 (2H), 2.03 (1H), 1.94 (2H), 1.54 (2H), 1.36 (4H), 1.33 (2H), 1.30 (2H), 1.29 (6H), 1.27 (4H), 1.26 (18H), 0.88 (9H).

$^{13}$C NMR (500 MHz, CDCl$_3$), δ178.4, 134.9, 129.3, 64.0, 57.6 (2C), 37.6, 34.0, 31.9 (2C), 31.9, 31.2, 29.9, 29.7, 29.7, 29.3 (4C), 29.3, 28.3 (2C), 27.5, 27.3 (2C), 22.7 (2C), 22.7, 14.1 (2C), 14.1.

Example 15

The present Example provides a compound I-15 represented by Formula I, which has a structural Formula as follows:

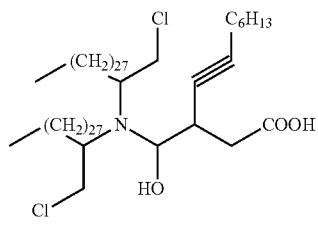

Formula I-15

Compound I-15 was prepared by the synthesis route as follows:

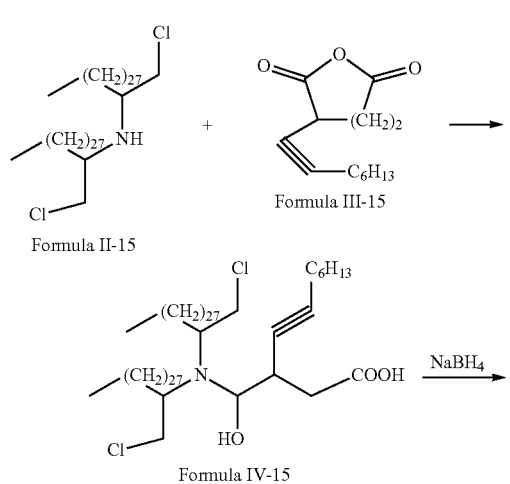

The synthesis method can be carried out with or without a solvent, and the synthesis method with a solvent was as follows:

(1) N,N-dialkyl secondary amine represented by Formula II-15 (92.8 g, 0.10 mol) was dissolved in toluene (20 mL) to obtain solution 1; decynyl butanedioic anhydride compound represented by Formula III-15 (22.2 g, 0.10 mol) was dissolved in toluene (30 mL) to obtain solution 2;

(2) the solution 1 was added into the solution 2, the thus obtained mixture was stirred while heating to 80° C. and then kept at 80° C. for 1 hour; after the reaction was finished, toluene was removed by concentrating in vacuum to obtain compound IV-15;

(3) compound IV-15 was reduced in tetrahydrofuran solution dissolved with sodium borohydride (NaBH$_4$) to obtain compound I-15.

In the present application, compound I-15 was analyzed by NMR:

$^1$H NMR (500 MHz, CDCl$_3$), δ12.01 (1H), 5.31 (1H), 4.60 (1H), 3.54 (4H), 2.84 (2H), 2.81 (1H), 2.46 (2H), 1.96 (2H), 1.44 (2H), 1.31 (4H), 1.29 (2H), 1.28 (4H), 1.26 (96H), 1.25 (8H), 0.88 (9H).

$^{13}$C NMR (500 MHz, CDCl$_3$), δ177.3, 86.5, 86.3, 80.8, 58.6 (2C), 50.9 (2C), 36.7, 31.9 (2C), 31.2 (2C), 30.9, 29.6 (44C), 29.3 (2C), 29.0, 28.1, 27.1, 26.5 (2C), 22.7 (2C), 22.7, 19.4, 14.1 (2C), 14.1.

Comparative Example 1

The present Example provides a compound I-d1 represented by Formula I, which has a structural Formula as follows:

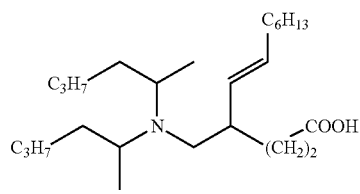

Compound I-d1 was prepared by the synthesis route as follows:

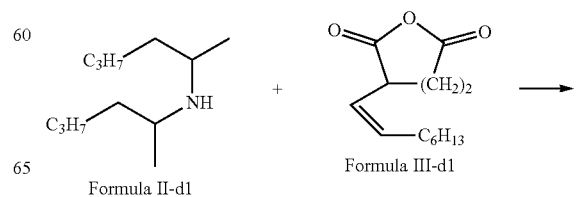

-continued

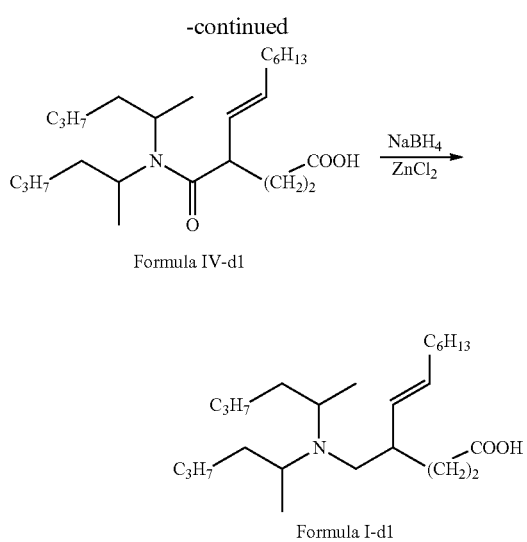

Formula IV-d1

Formula I-d1

The synthesis method was as follows:
(1) N,N-dialkyl secondary amine represented by Formula II-d1 (18.5 g, 0.10 mol) was dissolved in toluene (20 mL) to obtain solution 1; octenyl glutaric anhydride compound represented by Formula III-d1 (22.4 g, 0.10 mol) was dissolved in toluene (30 mL) to obtain solution 2;
(2) the solution 1 was added into the solution 2, and the thus obtained mixture was stirred while heating to 80° C. and then kept at 80° C. for 1 hour; after the reaction was finished, toluene was removed by concentrating in vacuum to obtain compound IV-d1;
(3) compound IV-d1 was reduced in tetrahydrofuran solution dissolved with sodium borohydride-zinc chloride (NaBH$_4$—ZnCl$_2$) to obtain compound I-d1.

In the present application, compound I-d1 was analyzed by NMR:
$^1$H NMR (500 MHz, CDCl$_3$), δ12.01 (1H), 5.48 (1H), 5.43 (1H), 2.63 (2H), 2.46 (2H), 2.33 (2H), 2.03 (1H), 1.94 (2H), 1.54 (2H), 1.33 (2H), 1.31 (12H), 1.29 (2H), 1.25 (4H), 1.06 (6H), 0.88 (9H).
$^{13}$C NMR (500 MHz, CDCl$_3$), δ178.4, 134.9, 129.3, 61.3 (2C), 59.0, 38.2, 34.6 (2C), 34.0, 31.9, 31.2, 29.9, 29.7 (2C), 29.4, 27.5, 22.7 (2C), 22.7, 21.0 (2C), 14.1 (2C), 14.1.

Comparative Example 2

The present Example provides a compound I-d2 represented by Formula I, which has a structural Formula as follows:

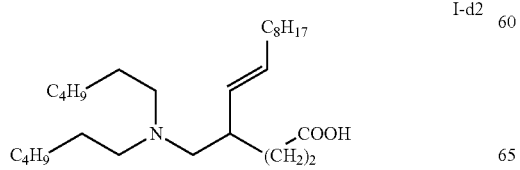

I-d2

Compound I-d2 was prepared by the synthesis route as follows:

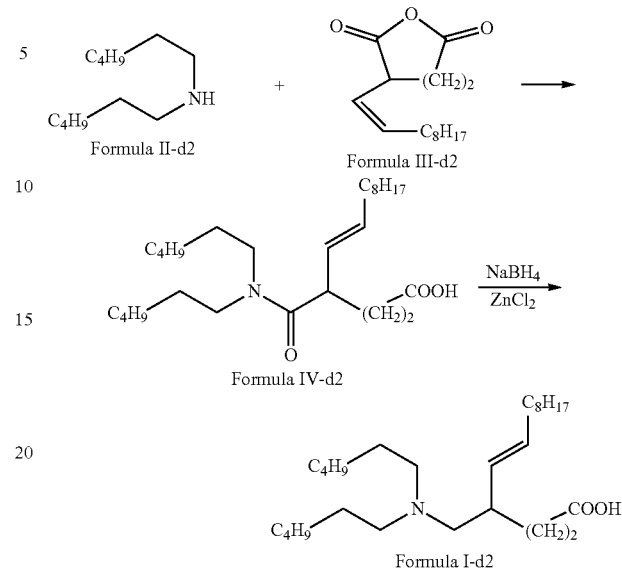

Formula II-d2

Formula III-d2

Formula IV-d2

Formula I-d2

The synthesis method was as follows:
(1) N,N-dihexyl secondary amine represented by Formula II-d2 (18.5 g, 0.10 mol) was dissolved in toluene (20 mL) to obtain solution 1; decenyl glutaric anhydride compound represented by Formula III-d2 (25.2 g, 0.10 mol) was dissolved in toluene (30 mL) to obtain solution 2;
(2) the solution 1 was added into the solution 2, and the thus obtained mixture was stirred while heating to 80° C. and then kept at 80° C. for 1 hour; after the reaction was finished, toluene was removed by concentrating in vacuum to obtain compound IV-d2;
(3) compound IV-d2 was reduced in tetrahydrofuran solution dissolved with sodium borohydride-zinc chloride (NaBH$_4$—ZnCl$_2$) to obtain compound I-d2.

In the present application, compound I-d2 was analyzed by NMR:
$^1$H NMR (500 MHz, CDCl$_3$), δ12.01 (1H), 5.48 (1H), 5.43 (1H), 2.46 (2H), 2.43 (4H), 2.33 (2H), 2.03 (1H), 1.94 (2H), 1.54 (2H), 1.36 (4H), 1.33 (2H), 1.30 (2H), 1.29 (6H), 1.28 (8H), 1.26 (6H), 0.88 (9H).
$^{13}$C NMR (500 MHz, CDCl$_3$), δ178.4, 134.9, 129.3, 64.0, 57.6 (2C), 37.6, 34.0, 31.9, 31.5 (2C), 31.2, 29.9, 29.7, 29.7, 29.3, 28.3 (2C), 27.5, 27.0 (2C), 22.7 (2C), 22.7, 14.1 (2C), 14.1.

Comparative Example 3

The present Example provides a compound I-d3 represented by Formula I, which has a structural Formula as follows:

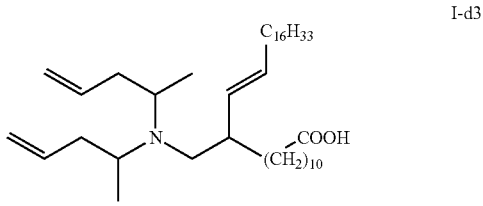

I-d3

Compound I-d3 was prepared by the synthesis route as follows:

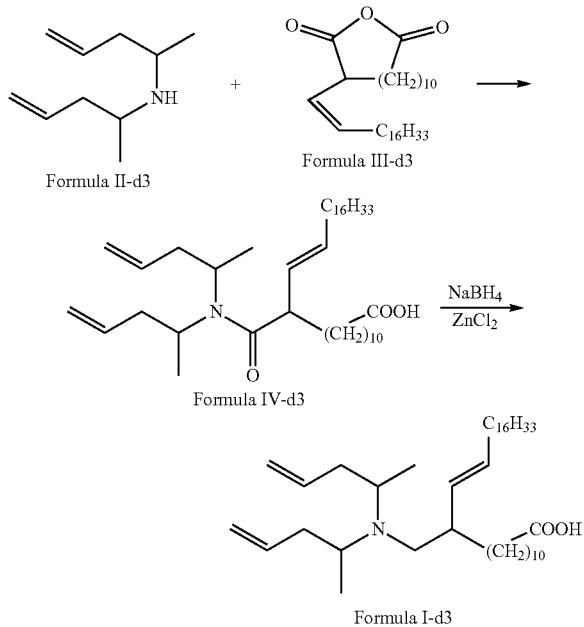

The synthesis method was as follows:
(1) N,N-dialkenyl secondary amine represented by Formula II-d3 (15.3 g, 0.10 mol) was dissolved in toluene (20 mL) to obtain solution 1; octadecenyl tridecanedioic anhydride compound represented by Formula III-d3 (47.6 g, 0.10 mol) was dissolved in toluene (30 mL) to obtain solution 2;
(2) the solution 1 was added into the solution 2, and the thus obtained mixture was stirred while heating to 80° C. and then kept at 80° C. for 1 hour; after the reaction was finished, toluene was removed by concentrating in vacuum to obtain compound IV-d3;
(3) compound IV-d3 was reduced in tetrahydrofuran solution dissolved with sodium borohydride-zinc chloride ($NaBH_4$—$ZnCl_2$) to obtain compound I-d3.

In the present application, compound I-d3 was analyzed by NMR:
$^1H$ NMR (500 MHz, $CDCl_3$), δ11.87 (1H), 5.82 (2H), 5.48 (1H), 5.43 (1H), 5.13 (2H), 4.88 (2H), 2.76 (2H), 2.46 (2H), 2.21 (2H), 2.13 (4H), 2.03 (1H), 1.94 (2H), 1.54 (2H), 1.33 (4H), 1.30 (4H), 1.29 (6H), 1.26 (26H), 1.25 (4H), 1.11 (6H), 0.88 (3H).
$^{13}C$ NMR (500 MHz, $CDCl_3$), δ178.4, 133.5, 133.0 (2C), 132.4, 115.8 (2C), 59.8 (2C), 59.5, 41.1 (2C), 38.8, 34.0, 34.0, 33.2, 31.9, 30.0, 29.9, 29.7, 29.7, 29.6 (3C), 29.6 (8C), 29.3, 29.3, 29.0, 27.2, 24.7, 22.7, 18.1 (2C), 14.1.

Test Example 1

Test for Enrichment of Rare Earth Elements.

(1) the compounds prepared in the above Examples 1 to 15 and Comparative Examples 1 to 3 were used in weight of (5.51, 6.24, 8.08, 11.52, 11.36, 6.91, 9.83, 9.44, 12.53, 10.96, 10.23, 10.98, 9.36, 6.42, 14.78 and 5.15, 5.51, 8.01) g, respectively;

(2) The above extractants were respectively mixed with 0.96 mL of 10.8 mol/L sodium hydroxide aqueous solution, and saponified at 25° C. for 5 min to obtain viscous liquid of saponified extractants with saponification degree of 80%;

(3) at room temperature, the viscous liquid of saponified extractants were mixed with 2000 mL of ion-type rare earth leaching solution for enrichment time of 0.5 h. Ion-type rare earth leaching solution contained 15 rare earth elements including lanthanum, cerium, praseodymium, neodymium, samarium, europium, gadolinium, terbium, dysprosium, holmium, erbium, thulium, ytterbium, lutetium and yttrium, with a total molar concentration of 0.00636 mol/L. pH=6.0 The concentration of rare earth ions in the water phase before and after enrichment was measured, and the total enrichment ratio of rare earth ions E % was calculated;

The specific test results (total enrichment ratio of rare earth ions) were shown in Table 1.

TABLE 1

| Item | Example 1 | Example 2 | Example 3 | Example 4 | Example 5 | Example 6 |
|---|---|---|---|---|---|---|
| Total enrichment ratio E % | 96.5 | 97.4 | 97.5 | 96.5 | 97.9 | 97.6 |

| Item | Example 7 | Example 8 | Example 9 | Example 10 | Example 11 | Example 12 |
|---|---|---|---|---|---|---|
| Total enrichment ratio E % | 97.7 | 97.9 | 97.9 | 96.6 | 95.9 | 98.5 |

| Item | Example 13 | Example 14 | Example 15 | Comparative Example 1 | Comparative Example 2 | Comparative Example 3 |
|---|---|---|---|---|---|---|
| Total enrichment ratio E % | 97.5 | 96.9 | 96.7 | 94.4 | 92.9 | 93.8 |

It can be seen from table 1 that the enrichment rate of N,N-dihydrocarbonyl amino carboxylic acid prepared according to the present application is over 95%, which can be used to enrich rare earth elements from raw materials containing low-concentration rare earth.

Test Example 2

Test for Separating Yttrium Ion
(1) the compounds prepared in the above Examples 1 to 15 and Comparative Example 1 were respectively prepared into extractant solutions; to be specific, the extractants prepared in Examples 1 to 15 and Comparative Examples 1 to 3 were taken in weight of 5.51 g, 6.24 g, 8.08 g, 11.52 g, 11.36 g, 6.91 g, 9.83 g, 9.44 g, 12.53 g, 10.96 g, 10.23 g, 10.98 g, 9.36 g, 6.42 g, 14.78 and 5.15 g, 5.51 g, 8.01 g, respectively; toluene was taken in weight of 19.5 g, 18.8 g, 16.9 g, 13.5 g, 13.6 g, 18.1 g, 15.2 g, 15.6 g, 12.5 g, 14.0 g, 14.8 g, 14.0 g, 15.6 g, 18.6 g, 10.2 g and 19.9 g, 19.5 g, 17.0 g respectively; the above two components were mixed to obtain extractant solutions with concentration of 0.52 mol/L and a total volume of 25 mL;

(2) the above extractant solutions were respectively mixed with 0.96 mL of 10.8 mol/L sodium hydroxide aqueous solution, and saponified at 25° C. for 5 min to obtain solution of saponified extractants with saponification degree of 80%;

(3) at room temperature, 25 mL of the saponified extractant solutions and 25 mL of mixed rare earth solution were mixed and extracted for 0.5 h. The mixed rare earth solution contained 15 rare earth elements including lanthanum, cerium, praseodymium, neodymium, samarium, europium, gadolinium, terbium, dysprosium, holmium, erbium, thulium, ytterbium, lutetium and yttrium, with a concentration of 0.020 mol/L for each element. The concentrations of rare earth ions in aqueous phase before and after extraction were measured, and the relative separation coefficient $\beta_{Ln/Y}$ of each rare earth ion (Ln) relative to yttrium ion (Y) was calculated;

The specific test results (relative separation coefficient $\beta_{Ln/Y}$ of rare earth ions (Ln) relative to yttrium ions (Y)) were shown in Table 2.

TABLE 2

| $\beta_{Ln/Y}$ | La/Y | Ce/Y | Pr/Y | Nd/Y | Sm/Y | Eu/Y | Gd/Y | Tb/Y | Dy/Y | Ho/Y | Er/Y | Tm/Y | Yb/Y | Lu/Y |
|---|---|---|---|---|---|---|---|---|---|---|---|---|---|---|
| Example 1 | 1.12 | 1.27 | 1.77 | 2.08 | 3.00 | 2.94 | 2.16 | 2.24 | 2.28 | 2.39 | 2.48 | 2.59 | 2.88 | 3.15 |
| Example 2 | 1.20 | 1.60 | 1.86 | 2.16 | 3.05 | 3.52 | 2.33 | 2.79 | 2.36 | 2.21 | 2.30 | 2.93 | 2.75 | 3.20 |
| Example 3 | 1.11 | 1.30 | 1.72 | 2.06 | 3.01 | 2.96 | 2.18 | 2.26 | 2.29 | 2.37 | 2.46 | 2.57 | 2.85 | 3.14 |
| Example 4 | 1.09 | 1.29 | 1.72 | 2.06 | 3.01 | 2.96 | 2.18 | 2.26 | 2.30 | 2.39 | 2.48 | 2.59 | 2.88 | 3.14 |
| Example 5 | 1.12 | 1.27 | 1.72 | 2.06 | 3.01 | 2.96 | 2.18 | 2.27 | 2.29 | 2.37 | 2.47 | 2.57 | 2.85 | 3.11 |
| Example 6 | 1.13 | 1.30 | 1.73 | 2.07 | 3.02 | 2.98 | 2.20 | 2.28 | 2.30 | 2.39 | 2.49 | 2.62 | 2.90 | 3.17 |
| Example 7 | 1.14 | 1.31 | 1.73 | 2.07 | 3.02 | 2.98 | 2.20 | 2.28 | 2.30 | 2.39 | 2.50 | 2.62 | 2.91 | 3.19 |
| Example 8 | 1.10 | 1.29 | 1.72 | 2.06 | 3.01 | 2.96 | 2.18 | 2.26 | 2.30 | 2.39 | 2.48 | 2.59 | 2.88 | 3.15 |
| Example 9 | 1.21 | 1.32 | 1.82 | 2.08 | 3.02 | 2.97 | 2.19 | 2.28 | 2.32 | 2.42 | 2.51 | 2.61 | 2.97 | 3.35 |
| Example 10 | 1.10 | 1.23 | 1.77 | 2.09 | 3.06 | 2.99 | 2.28 | 2.29 | 2.33 | 2.42 | 2.50 | 2.56 | 2.83 | 3.11 |
| Example 11 | 1.13 | 1.32 | 1.80 | 2.04 | 3.05 | 2.98 | 2.12 | 2.23 | 2.32 | 2.41 | 2.48 | 2.54 | 2.86 | 3.13 |
| Example 12 | 1.08 | 1.33 | 1.73 | 2.07 | 3.04 | 3.00 | 2.13 | 2.23 | 2.35 | 2.42 | 2.49 | 2.51 | 2.89 | 3.18 |
| Example 13 | 1.16 | 1.30 | 1.74 | 2.09 | 3.03 | 2.93 | 2.12 | 2.29 | 2.30 | 2.40 | 2.43 | 2.59 | 2.88 | 3.19 |
| Example 14 | 1.14 | 1.39 | 1.77 | 2.08 | 3.09 | 2.99 | 2.23 | 2.26 | 2.33 | 2.42 | 2.51 | 2.66 | 2.91 | 3.27 |
| Example 15 | 1.28 | 1.35 | 1.75 | 2.05 | 3.12 | 3.02 | 2.24 | 2.27 | 2.32 | 2.43 | 2.54 | 2.68 | 2.91 | 3.29 |
| Comparative Example 1 | 0.98 | 1.18 | 1.50 | 1.84 | 2.87 | 2.91 | 2.11 | 2.16 | 2.04 | 2.13 | 2.21 | 2.42 | 2.71 | 2.97 |
| Comparative Example 2 | 0.88 | 1.05 | 1.57 | 1.82 | 2.92 | 2.90 | 2.10 | 2.18 | 2.07 | 2.11 | 2.17 | 2.44 | 2.69 | 2.95 |
| Comparative Example 3 | 1.03 | 1.21 | 1.55 | 1.94 | 2.91 | 2.93 | 2.10 | 2.15 | 2.17 | 2.19 | 2.25 | 2.43 | 2.68 | 2.94 |

It can be seen from table 2 that the amino carboxylic acid provided in this application can be used to separate and purify yttrium from mixed rare earth raw materials.

Test Example 3

Stability Test

The stability of compound I-1 prepared in the above Example 1 was tested by the following procedure: compound I-1 was prepared into an extractant solution by dissolving 43.9 g of compound I-1 in 100 mL of toluene to prepare an extractant solution with a concentration of 1.0 mol/l; 50 mL of extractant solution and 50 mL of hydrochloric acid solution with concentration of 6 mol/L were mixed and stirred for 15 days, and another 50 mL of extractant solution and 50 mL of sodium hydroxide solution with concentration of 6 mol/L were mixed and stirred for 15 days, and then the extractant loss rate in both was tested by NMR.

The stability of compounds according to Examples 2 to 15 and Comparative Examples 1 to 3 was tested in the same manner as that of compound I-1;

Specific test results (the extractant loss rate in hydrochloric acid medium and liquid alkali medium) were shown in Table 3 below.

TABLE 3

| Item | extractant loss rate in hydrochloric acid medium (%) | extractant loss rate in liquid alkali medium (%) |
| --- | --- | --- |
| Example 1 | 0.03 | 0.05 |
| Example 2 | 0.03 | 0.04 |
| Example 3 | 0.03 | 0.04 |
| Example 4 | 0.03 | 0.04 |
| Example 5 | 0.03 | 0.04 |
| Example 6 | 0.04 | 0.05 |
| Example 7 | 0.03 | 0.05 |
| Example 8 | 0.04 | 0.05 |
| Example 9 | 0.03 | 0.05 |
| Example 10 | 0.03 | 0.05 |
| Example 11 | 0.03 | 0.05 |
| Example 12 | 0.03 | 0.05 |
| Example 13 | 0.03 | 0.05 |
| Example 14 | 0.03 | 0.05 |
| Example 15 | 0.03 | 0.04 |
| Comparative | 0.06 | 0.07 |
| Comparative | 0.06 | 0.07 |
| Comparative | 0.06 | 0.07 |

It can be seen from table 3 that the loss rate of N,N-dihydrocarbonyl amino carboxylic acid in hydrochloric acid medium was below 0.04%; and the loss rate in caustic soda liquid was below 0.05%. Therefore, the N,N-dihydrocarbonyl amino carboxylic acids prepared by the present application have excellent chemical stability and can withstand strong acid and strong alkali without decomposition.

The applicant declares that the N,N-dihydrocarbonyl amino carboxylic acid and its preparation method and use according to the present application are illustrated by the above Examples, but the present application is not limited to the above Examples, which does not mean that the present application should be implemented only by relying on the above Examples. The protection scope of this application is defined by the claims.

The invention claimed is:

1. An N,N-dihydrocarbonyl amino carboxylic acid with a structure represented by Formula I:

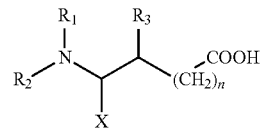

Formula I wherein, $R_1$ and $R_2$ are each independently a linear or branched, saturated or unsaturated, and unsubstituted C7-C30 alkyl, alkenyl or alkynyl, or a linear or branched, saturated or unsaturated, and substituted C7-C30 alkyl, alkenyl or alkynyl, wherein the substituents of the alkyl, alkenyl or alkynyl are each independently any one or a combination of at least two selected from the group consisting of halogen, hydroxyl, carboxyl, phenyl, phenoxy, amino, nitro, cyano and thiol;

$R_3$ is a linear or branched, saturated or unsaturated, and unsubstituted C6-C30 alkyl, alkenyl or alkynyl, or a linear or branched, saturated or unsaturated, and substituted C6-C30 alkyl, alkenyl or alkynyl, wherein the substituents of the alkyl, alkenyl or alkynyl are each independently any one or a combination of at least two selected from the group consisting of halogen, hydroxyl, carboxyl, phenyl, phenoxy, amino, nitro, cyano and thiol;

X is H or OH; and n is a natural number from 1 to 10.

2. The N,N-dihydrocarbonyl amino carboxylic acid according to claim 1, wherein, $R_1$ and $R_2$ are each independently a linear or branched, saturated or unsaturated, and unsubstituted C7-C18 alkyl, alkenyl or alkynyl, or a linear or branched, saturated or unsaturated, and substituted C7-C18 alkyl, alkenyl or alkynyl.

3. The N,N-dihydrocarbonyl amino carboxylic acid according to claim 1, wherein, $R_1$ and $R_2$ are each independently a linear, saturated or unsaturated, and unsubstituted C7-C30 alkyl, alkenyl or alkynyl.

4. The N,N-dihydrocarbonyl amino carboxylic acid according to claim 1, wherein, $R_1$ and $R_2$ are each independently a branched, saturated or unsaturated, and unsubstituted C7-C30 alkyl, alkenyl or alkynyl.

5. The N,N-dihydrocarbonyl amino carboxylic acid according to claim 1, wherein, $R_1$ and $R_2$ are each independently a branched, saturated or unsaturated, and unsubstituted C7-C17 alkyl, alkenyl or alkynyl.

6. The N,N-dihydrocarbonyl amino carboxylic acid according to claim 5, wherein, $R_1$ and $R_2$ are each independently a linear or branched and unsubstituted C7-C30 alkyl.

7. The N,N-dihydrocarbonyl amino carboxylic acid according to claim 1, wherein, $R_1$ and $R_2$ are each independently a linear or branched and unsubstituted C7-C18 alkyl.

8. The N,N-dihydrocarbonyl amino carboxylic acid according to claim 1, wherein, $R_1$ and $R_2$ are each independently a linear or branched and unsubstituted C7-C10 alkyl.

9. The N,N-dihydrocarbonyl amino carboxylic acid according to claim 1, wherein X is H.

10. The N,N-dihydrocarbonyl amino carboxylic acid according to claim 1, wherein $R_1$ and $R_2$ are independently

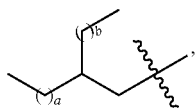

wherein 3≤a+b≤10, represents a connecting site.

11. The N,N-dihydrocarbonyl amino carboxylic acid according to claim 1, wherein $R_1$ and $R_2$ are independently any one selected from the group consisting of the following groups, wherein ⸾ represents a connecting site,

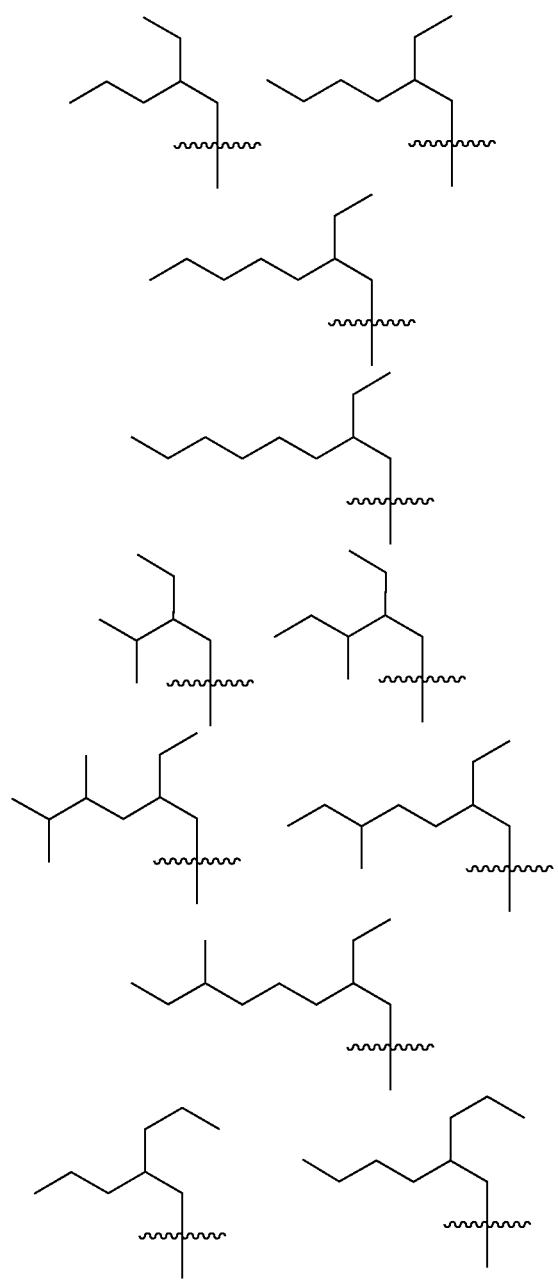

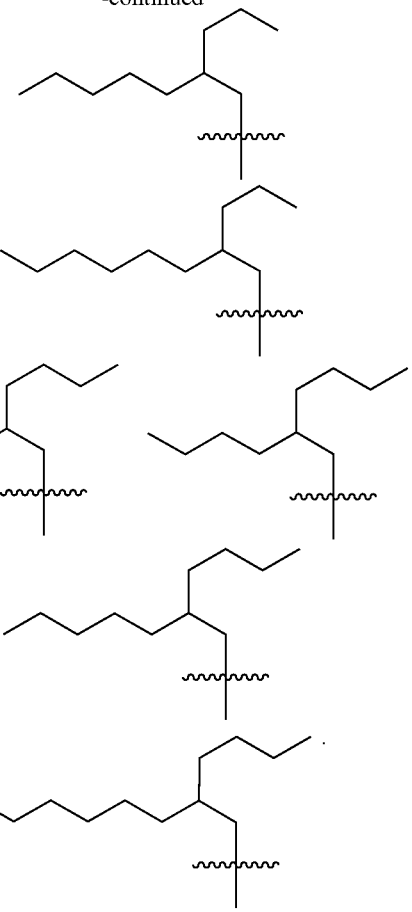

12. The N,N-dihydrocarbonyl amino carboxylic acid according to claim 2, wherein, $R_3$ is selected from a linear or branched, unsaturated, and unsubstituted C6-C30 alkenyl or alkynyl.

13. The N,N-dihydrocarbonyl amino carboxylic acid according to claim 1, wherein, $R_3$ is a linear C10-C30 alkenyl.

14. The N,N-dihydrocarbonyl amino carboxylic acid according to claim 1, wherein, $R_3$ is a linear C10-C18 alkenyl.

15. The N,N-dihydrocarbonyl amino carboxylic acid according to claim 1, wherein $R_3$ is any one selected from the group consisting of the following groups, wherein ⸾ represents a connecting site,

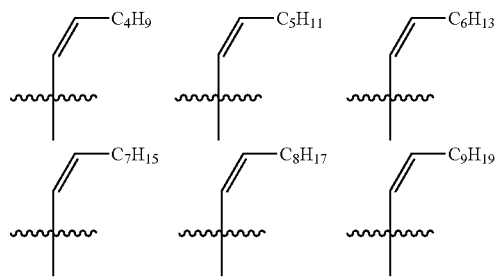

-continued

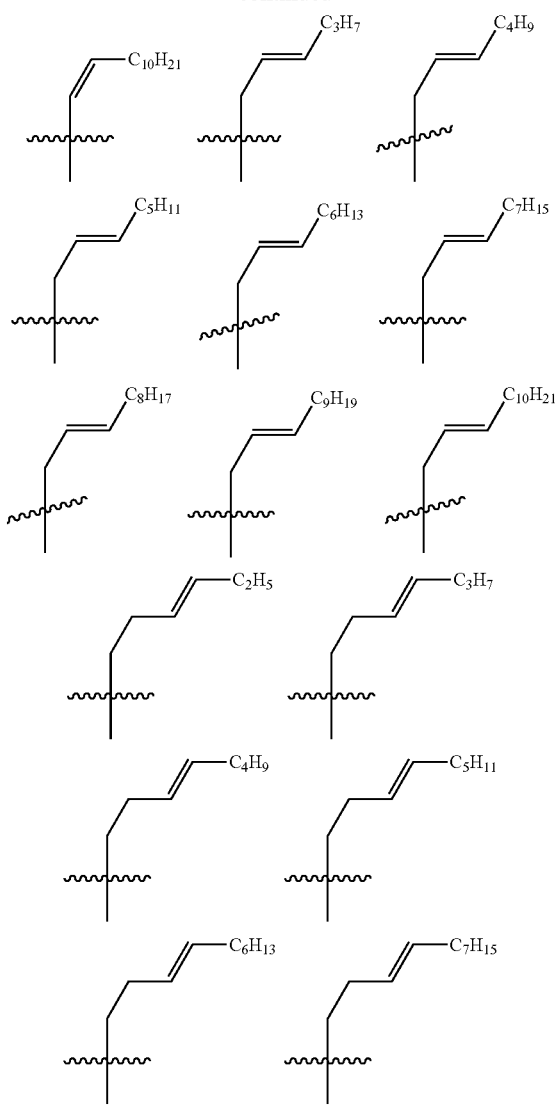

16. A method for preparing the N, N-dihydrocarbonyl amino carboxylic acid according to claim 1 comprising steps of:
mixing and reacting N, N-dihydrocarbonyl secondary amine represented by Formula II and anhydride compound represented by Formula III to obtain N, N-dihydrocarbonyl amide carboxylic acid represented by Formula IV, and then reducing the N, N-dihydrocarbonyl amide carboxylic acid represented by Formula IV with reducing agent to obtain the N, N-dihydrocarbonyl amino carboxylic acid represented by Formula I, as shown in the following Reaction Scheme

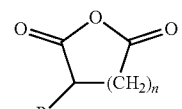
Formula II

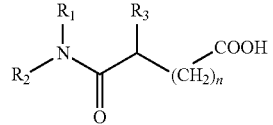
Formula III

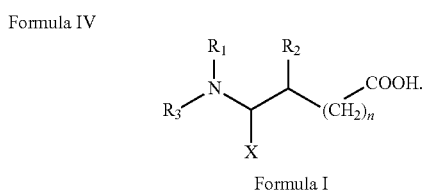
Formula IV

Reducing agent →

$$\begin{array}{c} R_1 \quad R_2 \\ N \\ R_3 \quad \quad \text{COOH.} \\ X \quad (CH_2)_n \end{array}$$
Formula I 17. The method for preparing the N,N-dihydrocarbonyl amino carboxylic acid according to claim 16, wherein a molar ratio between the N,N-dihydrocarbonyl secondary amine represented by Formula II and the anhydride compound represented by Formula III is 1: (0.8-1.2).

18. The method for preparing the N,N-dihydrocarbonyl amino carboxylic acid according to claim 16, wherein the N,N-dihydrocarbonyl secondary amine represented by Formula II and the anhydride compound represented by Formula III are mixed and reacted at temperature of 0° C. to 125° C. for 0.5 to 4 hours.

19. The method for preparing the N,N-dihydrocarbonyl amino carboxylic acid according to claim 16, wherein the N,N-dihydrocarbonyl secondary amine represented by Formula II and the anhydride compound represented by Formula III are mixed and reacted in the absence of a solvent.

20. The method for preparing the N,N-dihydrocarbonyl amino carboxylic acid according to claim 16, wherein the N,N-dihydrocarbonyl secondary amine represented by Formula II and the anhydride compound represented by Formula III are mixed and reacted in a solvent.

21. The method for preparing the N,N-dihydrocarbonyl amino carboxylic acid according to claim 20, wherein the solvent is an inert solvent selected from any one or a combination of at least two selected from the group consisting of hexane, dichloromethane, petroleum ether, toluene, xylene or kerosene.

22. The N,N-dihydrocarbonyl amino carboxylic acid according to claim 9, wherein n is a natural number from 1 to 6.

23. The N,N-dihydrocarbonyl amino carboxylic acid according to claim 5, wherein, $R_1$ and $R_2$ are each independently a branched, saturated or unsaturated, and unsubstituted C7-C12 hydrocarbonyl.

* * * * *